United States Patent
Jeong et al.

(10) Patent No.: US 11,267,852 B2
(45) Date of Patent: Mar. 8, 2022

(54) CELL LINES FOR SCREENING ODORANT AND AROMA RECEPTORS

(71) Applicant: Firmenich SA, Satigny (CH)

(72) Inventors: Hyo-Young Jeong, Woodside, NY (US); Patrick Pfister, Brooklyn, NY (US); Matthew Rogers, Briarcliff Manor, NY (US)

(73) Assignee: FIRMENICH SA, Geneva (CH)

( * ) Notice: Subject to any disclaimer, the term of this patent is extended or adjusted under 35 U.S.C. 154(b) by 232 days.

(21) Appl. No.: 15/580,110

(22) PCT Filed: Jun. 9, 2016

(86) PCT No.: PCT/US2016/036777
§ 371 (c)(1),
(2) Date: Dec. 6, 2017

(87) PCT Pub. No.: WO2016/201153
PCT Pub. Date: Dec. 15, 2016

(65) Prior Publication Data
US 2018/0298069 A1    Oct. 18, 2018

Related U.S. Application Data

(60) Provisional application No. 62/221,580, filed on Sep. 21, 2015, provisional application No. 62/173,762, filed on Jun. 10, 2015.

(51) Int. Cl.
| | |
|---|---|
| *C12N 5/00* | (2006.01) |
| *C07K 14/47* | (2006.01) |
| *C12N 5/10* | (2006.01) |
| *C12N 15/85* | (2006.01) |
| *C07K 14/705* | (2006.01) |
| *C12N 9/22* | (2006.01) |
| *C12N 15/11* | (2006.01) |
| *C12N 15/86* | (2006.01) |
| *G01N 33/50* | (2006.01) |

(52) U.S. Cl.
CPC .......... *C07K 14/4705* (2013.01); *C07K 14/47* (2013.01); *C07K 14/705* (2013.01); *C12N 5/10* (2013.01); *C12N 9/22* (2013.01); *C12N 15/11* (2013.01); *C12N 15/85* (2013.01); *C12N 15/86* (2013.01); *G01N 33/502* (2013.01); *C12N 2310/20* (2017.05); *C12N 2510/02* (2013.01); *C12N 2800/80* (2013.01); *C12N 2830/00* (2013.01); *G01N 2333/705* (2013.01); *G01N 2500/10* (2013.01)

(58) Field of Classification Search
USPC .......................................................... 435/325
See application file for complete search history.

(56) References Cited

U.S. PATENT DOCUMENTS

| | | |
|---|---|---|
| 7,425,445 B2 | 9/2008 | Matsunami et al. |
| 2006/0179501 A1* | 8/2006 | Chan .................. A01K 67/0275 800/18 |

FOREIGN PATENT DOCUMENTS

| | | | |
|---|---|---|---|
| JP | WO 2015/020158 | * | 2/2015 |
| WO | 2013082522 A1 | | 6/2013 |
| WO | WO 2013/082522 | * | 6/2013 |
| WO | 2015020158 A1 | | 2/2015 |

OTHER PUBLICATIONS

Saito (Nature Neuroscience, May 2014, vol. 17, No. 5, p. 661-663).*
Garanto (PLoS, Nov. 2013, vol. 8, No. 11, e79369, p. 1-10).*
English translation of Touhara WO 2015/020158, 2015.*
Maeder (Nature Methods, 2013, vol. 10, No. 10, p. 977-979).*
Zhuang (Nature Protocols, 2008, vol. 3, No. 9, p. 1402-1413).*
Qin (PLoS, 2010, vol. 5, No. 5, e10611).*
International Search Report and Written Opinion, for application No. PCT/US2016/036777 dated Sep. 5, 2016.
Kyte & Doolittle, "A Simple Method of Displaying the Hydropathic Character of a Protein", Journal of Molecular Biology, vol. 157, p. 105-32, 1982.
Morgan Maeder et al., "CRISPR RNA-guided activation of endogenous human genes," Nature Methods, vol. 10, No. 10, p. 977-979, 2013.
Albert Cheng et al., "Multiplexed activation of endogenous genes by CRISPR-on, an RNA-guided transcriptional activator system," Cell Research, vol. 23, p. 1163-1171, 2013.

* cited by examiner

*Primary Examiner* — Michael C Wilson
(74) *Attorney, Agent, or Firm* — Armstrong Teasdale LLP

(57) ABSTRACT

Provided herein is a cell line with improved odorant receptor function comprising an activated endogenous RTP1 gene, which further expresses an RTP1 protein. Further provided herein is a method for specifically activating an endogenous RTP1 gene in a eukaryotic cell using a CRISPR/Cas9 derived technique. Also provided herein is a method for identifying compounds with desired effects such as perfume or aroma modulators in said cell line.

13 Claims, 6 Drawing Sheets
Specification includes a Sequence Listing.

SEQUENCE LISTING

```
<160> NUMBER OF SEQ ID NOS: 20

<210> SEQ ID NO 1
<211> LENGTH: 21
<212> TYPE: DNA
<213> ORGANISM: artificial
<220> FEATURE:
<223> OTHER INFORMATION: Guide RNA target sequence

<400> SEQUENCE: 1
ctgcaatctc agttcagggc c                                            21

<210> SEQ ID NO 2
<211> LENGTH: 3628
<212> TYPE: DNA
<213> ORGANISM: artificial
<220> FEATURE:
<223> OTHER INFORMATION: Donor DNA for homology directed repair
```

<400> SEQUENCE: 2

| | | | | | |
|---|---|---|---|---|---|
| ggggttttat | ggaagagtct | tacttctctt | ttctttcatc | tatattttgt | atttttcta | 60 |
| gaataaaccc | atatgatttt | ttaaaaggaa | aaataattta | ttaaaaatag | cagcagaggc | 120 |
| atgtatagta | aaggctgttt | tgcctgtggg | tggtgctcct | cttctgcgct | tctataatca | 180 |
| gcttggaaat | aatcttgtct | gctcctgcct | ggctgatgca | atgctcctac | ctttgtgcac | 240 |
| aggtggctgt | tcttgcacaa | ggccattgca | gcatggatcc | tattgcacag | ttattcagta | 300 |
| cacagtcagc | tacaagcact | gacatagagc | ttggcacatg | tctgcaaacc | ctacccacat | 360 |
| gctcggatat | gtttgaaatg | aatgaattaa | tgaaccggtc | tggggtcaac | agcttgaatt | 420 |
| tgtatacagg | ctccgccatt | tataggctag | gtgagtccta | ggctcctgat | ctgtactgca | 480 |
| gcaatagtaa | tcataactta | agagacctcc | aattgtgttt | tgaaaatggc | aaagtgctgg | 540 |
| tcacaagatg | gctggggaag | ccgagagaga | gtttattatt | attgctccat | ctactaacaa | 600 |
| atttacatct | ccccatccct | catttctcct | tggctgccta | aggcatcatg | gttaccgtag | 660 |
| cagccagatg | ctgatgatgc | ctccagggga | cggcaaggtg | aaactgagcc | agttcccagt | 720 |
| cctcacctcc | ccatactctt | tccaggccag | ggtgagatgg | tctgaagctc | agtctctggt | 780 |
| caggtccccc | actctgtctt | ggatcattta | gacccgcggc | cgcggcgcgc | ctcggaattc | 840 |
| gattgaagtt | cctattccga | agttcctatt | ctctagaaag | tataggaact | cggtgtgga | 900 |
| aagtccccag | gctccccagc | aggcagaagt | atgcaaagca | tgcatctcaa | ttagtcagca | 960 |
| accatagtcc | cgcccctaac | tccgcccatc | ccgcccctaa | ctccgcccag | ttccgcccat | 1020 |
| tctccgcccc | atggctgact | aattttttt | atttatgcag | aggccgaggc | cgcctcggcc | 1080 |
| tctgagctat | tccagaagta | gtgaggaggc | ttttttggag | gcctaggctt | ttgcaaaaag | 1140 |
| cttgcatgcc | tgcaggtcgg | ccgccacgac | cggtgccgcc | accatcccct | gacccacgcc | 1200 |
| cctgaccct | cacaaggaga | cgaccttcca | tgaccgagta | caagcccacg | gtgcgcctcg | 1260 |
| ccacccgcga | cgacgtcccc | cgggccgtac | gcaccctcgc | cgccgcgttc | gccgactacc | 1320 |
| ccgccacgcg | ccacaccgtc | gacccggacc | gccacatcga | gcgggtcacc | gagctgcaag | 1380 |
| aactcttcct | cacgcgcgtc | gggctcgaca | tcggcaaggt | gtgggtcgcg | gacgacggcg | 1440 |
| ccgcggtggc | ggtctggacc | acgccggaga | gcgtcgaagc | gggggcggtg | ttcgccgaga | 1500 |
| tcggcccgcg | catggccgag | ttgagcggtt | cccggctggc | cgcgcagcaa | cagatggaag | 1560 |
| gcctcctggc | cccgcaccgg | cccaaggagc | ccgcgtggtt | cctggccacc | gtcggcgtct | 1620 |
| cgcccgacca | ccagggcaag | ggtctgggca | gcgccgtcgt | gctccccgga | gtggaggcgg | 1680 |
| ccgagcgcgc | cggggtgccc | gccttcctgg | agacctccgc | gccccgcaac | ctcccctct | 1740 |
| acgagcggct | cggcttcacc | gtcaccgccg | acgtcgaggt | gcccgaagga | ccgcgcacct | 1800 |
| ggtgcatgac | ccgcaagccc | ggtgcctgac | gcccgcccca | cgacccgcag | cgcccgaccg | 1860 |
| aaaggagcgc | acgaccccat | ggctccgacc | gaagccaccc | ggggcggccc | cgccgacccc | 1920 |
| gcacccgccc | ccgaggccca | ccgactctag | aggatcataa | tcagccatac | cacatttgta | 1980 |
| gaggttttac | ttgctttaaa | aaacctccca | cacctccccc | tgaacctgaa | acataaaatg | 2040 |
| aatgcaattg | ttgttgttaa | cttgtttatt | gcagcttata | atggttacaa | ataaagcaat | 2100 |
| agcatcacaa | atttcacaaa | taaagcattt | ttttcactgc | aagttccta | ttccgaagtt | 2160 |
| cctattctct | agaaagtata | ggaacttcaa | tcactagtga | attcacgcgt | tgacattgat | 2220 |
| tattgactag | ttattaatag | taatcaatta | cggggtcatt | agttcatagc | ccatatatgg | 2280 |

```
agttccgcgt tacataactt acggtaaatg gcccgcctgg ctgaccgccc aacgaccccc    2340
gcccattgac gtcaataatg acgtatgttc ccatagtaac gccaatcggg actttccatt    2400
gacgtcaatg ggtggagtat ttacggtaaa ctgcccactt ggcagtacat caagtgtatc    2460
atatgccaag tacgccccct attgacgtca atgacggtaa atggcccgcc tggcattatg    2520
cccagtacat gaccttatgg gactttccta cttggcagta catctacgta ttagtcatcg    2580
ctattaccat ggtgatgcgg ttttggcagt acatcaatgg gcgtggatag cggtttgact    2640
cacggggatt tccaagtctc cacccccattg acgtcaatgg gagtttgttt tggcaccaaa    2700
atcaacggga ctttccaaaa tgtcgtaaca actccgcccc attgacgcaa atgggcggta    2760
ggcgtgtacg gtgggaggtc tatataagca gagctcgttt agtgaaccgt gtttaaacct    2820
cttcagagac tccctcctcc ccaagctctg tcttctggca acctgcctgg ttgccgtgga    2880
aacaggttcc actgcggaca aaggagggag ctgggtcctg cttcctcctg gtcttgtcga    2940
tgaggatttt tagaccgtgg agactgcgct gccctgccct gcacctaccc tcactctccg    3000
tgttctcact aaggtggaaa ttgccttccc tcactactga cgagaccatg tgtaaaagcg    3060
tgaccacaga tgagtggaag aaagtcttct atgagaagat ggaggaggca aagccggctg    3120
acagctggga cctcatcata gaccccaacc tcaagcacaa tgtgctgagc cctggttgga    3180
agcagtacct ggaattgcat gcttcaggca ggtgagtagc ccaggaaagt ggatccctgc    3240
aggccgcctc taggtcccta gctctggggc accttccaag gagaggaaga ttacgtagaa    3300
cccaagtgtt tagcttcaat ctcactatta ggctggcgta gactggaagt cagagaaaga    3360
gtccctaact gggaactacg acacttgagt tggatttcag ctcttctact gatcacctgt    3420
gttactcttc ctctctgagt cacaattttt ccgtctggaa aataaagaca tagaatatac    3480
gtatgagtcc tacacactga cattttacat attttctatt ttaacagtct cttaaaaagt    3540
agtttaaaac cagagaagaa gggtttgagg cccactgggg gtcgagacgt ccgtgctctg    3600
gtcctgggac cggtttaaat ctatttaa                                       3628
```

<210> SEQ ID NO 3
<211> LENGTH: 928
<212> TYPE: DNA
<213> ORGANISM: mouse

<400> SEQUENCE: 3

```
atgaaaaccc tcagcagccc cagcaactcc agcaccatca ctggcttcat cctcttgggc      60
ttcgcctacc ccagggaggg gcaaattctc ctctttgtga tcttcttcat tgtttacata     120
ctcattctta tgggcaacgc ttccatcatc tgtgctgtgt actgtgatca gagactccac     180 accccccatgt accttctgct ggccaacttc tccttcatgg agattggata tgtcacctcc     240
acagtcccca acatgttggc caacttcctt tcagacacca aggtcatctc tttctctgga     300
tgcttcctgc agttctattt cttcttctcc tttggttcta cagaatgctt tttcctggca     360 gtcatgggcat ttgatcgata ccttgccatc tgtaggccac tacattatcc ttctctcatg     420
actgggcgcc tccgaaacac ccttgtgacc agttgctggg tgcttggttt cctctggttc     480
cctgtaccca tcatcatcat ctcccagatg tccttctgtg gtccagaat tatagaccac     540 ttcctgtgtg acccaggccc tcttttggcc cttgctgtt ccagagtccc attgatagag     600
gttttctggt ccattataat gtctatgctc ctggttattc ctttcctctt catcatggga     660
acttacatat tggtcctaag agctgtgttt agacttcctt caagagaagg acaaaaaaag     720 gcttctctcca cttgcgggtc tcatctcaca gtagtttcac tctttattg ctcagtgatg     780
```

```
ataatgtatc tgagcccaac atctgagcat gaggccggaa tgcagaagct tgtaactcta    840 tttattctg tgggtacacc actgcttaat cctatgatat acagtctgag gaacaaagat    900
atgaaaaatg ccctacagaa gattttga                                      928
```

<210> SEQ ID NO 4
<211> LENGTH: 311
<212> TYPE: PRT
<213> ORGANISM: mouse

<400> SEQUENCE: 4

```
Met Lys Thr Leu Ser Ser Pro Ser Asn Ser Thr Ile Thr Gly Phe
1               5                   10                  15

Ile Leu Leu Gly Phe Ala Tyr Pro Arg Glu Gly Gln Ile Leu Leu Phe
            20                  25                  30

Val Ile Phe Phe Ile Val Tyr Ile Leu Ile Leu Met Gly Asn Ala Ser
        35                  40                  45

Ile Ile Cys Ala Val Tyr Cys Asp Gln Arg Leu His Thr Pro Met Tyr
    50                  55                  60

Leu Leu Leu Ala Asn Phe Ser Phe Met Glu Ile Gly Tyr Val Thr Ser
65                  70                  75                  80

Thr Val Pro Asn Met Leu Ala Asn Phe Leu Ser Asp Thr Lys Val Ile
                85                  90                  95

Ser Phe Ser Gly Cys Phe Leu Gln Phe Tyr Phe Phe Ser Phe Gly
            100                 105                 110

Ser Thr Glu Cys Phe Phe Leu Ala Val Met Ala Phe Asp Arg Tyr Leu
        115                 120                 125

Ala Ile Cys Arg Pro Leu His Tyr Pro Ser Leu Met Thr Gly Arg Leu
    130                 135                 140

Arg Asn Thr Leu Val Thr Ser Cys Trp Val Leu Gly Phe Leu Trp Phe
145                 150                 155                 160

Pro Val Pro Ile Ile Ile Ser Gln Met Ser Phe Cys Gly Ser Arg
                165                 170                 175

Ile Ile Asp His Phe Leu Cys Asp Pro Gly Pro Leu Leu Ala Leu Ala
            180                 185                 190

Cys Ser Arg Val Pro Leu Ile Glu Val Phe Trp Ser Ile Ile Met Ser
        195                 200                 205

Met Leu Leu Val Ile Pro Phe Leu Phe Ile Met Gly Thr Tyr Ile Leu
    210                 215                 220

Val Leu Arg Ala Val Phe Arg Leu Pro Ser Arg Glu Gly Gln Lys Lys
225                 230                 235                 240

Ala Phe Ser Thr Cys Gly Ser His Leu Thr Val Val Ser Leu Phe Tyr
                245                 250                 255

Cys Ser Val Met Ile Met Tyr Leu Ser Pro Thr Ser Glu His Glu Ala
            260                 265                 270

Gly Met Gln Lys Leu Val Thr Leu Phe Tyr Ser Val Gly Thr Pro Leu
        275                 280                 285

Leu Asn Pro Met Ile Tyr Ser Leu Arg Asn Lys Asp Met Lys Asn Ala
    290                 295                 300

Leu Gln Lys Ile Leu Arg Thr
305                 310
```

<210> SEQ ID NO 5
<211> LENGTH: 936
<212> TYPE: DNA

<213> ORGANISM: mouse

<400> SEQUENCE: 5

```
atgaaaaccc tcagcagccc cagcaactcc agcaccatca ctggcttcat cctcttgggc     60
ttcccctgcc ccagggaggg gcaaatcctc ctctttgtga ccttcttcat tgtttacata    120
ctcattctta tgggcaatgc ttccatcatc tgtgctgtgt actgtgatca gagcctccac    180
accccatgt  acttcctgct ggccaacttc tccttcctgg agatctggta tgtcacctcc    240
acagtcccca catgttggc  caacttcctt tcagacacca aggtcatctc tttctctgga    300
tgcttcctgc agttctattt cttcttctcc tttggttcta cagaatgctt tttcctggca    360
gtcatggcat ttgatcgata ccttgccatc tgtaggccac tacattatcc ttctctcatg    420
actgggcacc tctgcaacat ccttgtgatc agttgctggg tgcttggttt cctctggttc    480
cctgtaccca tcatcatcat ctcccagatg tccttctgtg ggtccagaat tatagaccac    540
ttcctgtgtg acccaggccc tcttttggcc cttgcctgtt ccagagcccc attgatggag    600
gttttctgga caattataat gtctatgctc ctggttattc ctttcctctt catcatggga    660
acttacatat tggtcctaag agctgtgttt agacttcctt caagagatgg acaaaaaaag    720
gccttctcca cttgcgggtc tcatctcaca gtagtttcac tcttttattg ctcagtgatg    780
aaaatgtatt tgagcccaac atctgagcat gaagctggaa tgcagaagct tgtaactcta    840
ttttattctg tgggtactcc actacttaat cctgtgatat acagtctgag gaacaaagat    900
atgaaaaatg ccctgcagaa gattttaaga acataa                             936
```

<210> SEQ ID NO 6
<211> LENGTH: 311
<212> TYPE: PRT
<213> ORGANISM: mouse

<400> SEQUENCE: 6

```
Met Lys Thr Leu Ser Ser Pro Ser Asn Ser Ser Thr Ile Thr Gly Phe
1               5                   10                  15

Ile Leu Leu Gly Phe Pro Cys Pro Arg Glu Gly Gln Ile Leu Leu Phe
            20                  25                  30

Val Thr Phe Phe Ile Val Tyr Ile Leu Ile Leu Met Gly Asn Ala Ser
        35                  40                  45

Ile Ile Cys Ala Val Tyr Cys Asp Gln Ser Leu His Thr Pro Met Tyr
    50                  55                  60

Phe Leu Leu Ala Asn Phe Ser Phe Leu Glu Ile Trp Tyr Val Thr Ser
65                  70                  75                  80

Thr Val Pro Asn Met Leu Ala Asn Phe Leu Ser Asp Thr Lys Val Ile
                85                  90                  95

Ser Phe Ser Gly Cys Phe Leu Gln Phe Tyr Phe Phe Ser Phe Gly Ser
            100                 105                 110

Ser Thr Glu Cys Phe Phe Leu Ala Val Met Ala Phe Asp Arg Tyr Leu
        115                 120                 125

Ala Ile Cys Arg Pro Leu His Tyr Pro Ser Leu Met Thr Gly His Leu
    130                 135                 140

Cys Asn Ile Leu Val Ile Ser Cys Trp Val Leu Gly Phe Leu Trp Phe
145                 150                 155                 160

Pro Val Pro Ile Ile Ile Ile Ser Gln Met Ser Phe Cys Gly Ser Arg
                165                 170                 175

Ile Ile Asp His Phe Leu Cys Asp Pro Gly Pro Leu Leu Ala Leu Ala
            180                 185                 190
```

Cys Ser Arg Ala Pro Leu Met Glu Val Phe Trp Thr Ile Ile Met Ser
            195                 200                 205

Met Leu Leu Val Ile Pro Phe Leu Phe Ile Met Gly Thr Tyr Ile Leu
    210                 215                 220

Val Leu Arg Ala Val Phe Arg Leu Pro Ser Arg Asp Gly Gln Lys Lys
225                 230                 235                 240

Ala Phe Ser Thr Cys Gly Ser His Leu Thr Val Val Ser Leu Phe Tyr
            245                 250                 255

Cys Ser Val Met Lys Met Tyr Leu Ser Pro Thr Ser Glu His Glu Ala
            260                 265                 270

Gly Met Gln Lys Leu Val Thr Leu Phe Tyr Ser Val Gly Thr Pro Leu
            275                 280                 285

Leu Asn Pro Val Ile Tyr Ser Leu Arg Asn Lys Asp Met Lys Asn Ala
            290                 295                 300

Leu Gln Lys Ile Leu Arg Thr
305                 310

<210> SEQ ID NO 7
<211> LENGTH: 942
<212> TYPE: DNA
<213> ORGANISM: mouse

<400> SEQUENCE: 7

```
atgggaatcc tttccacagg aaatcaaact gtcactgagt ttgtacttct tggtttccat     60
gaagtccctg gctgcacct  cctgtttttt tctgtgttca ccatcctcta tgcctccatc    120
atcacaggga acatgctcat tgcagtggtg gtggtgagct cccagaggct tcacacaccc    180
atgtatttct ttctggtgaa tctgtccttc atagagattg tctataccct cacagtggtg    240
cccaaaatgc tggaaggctt cttacaggag gccaccatat ctgtggctgg ctgcttgctc    300
cagttctttg tttttggctc tctggccaca gatgagtgtt ttctgctggc tgtgatggca    360
tatgatcgat atctcgcaat tgtcaccct  ctacgatacc cacacctcat ggggcctcaa    420
tggtgcctgg ggttggtgct acagtctgg  ctgtctggct tcatggtaga tggactagtt    480
gttgctctga tggcccagtt gagattctgt ggccccaact tagttgatca ctttttactgt    540
gatttttcac ctttgatggt cctggcttgc tcagatacccc aagtggccca ggtgactaca    600
tttgttctct ctgtggtctt cctgactgtc ccctttgggc tggttctgat ctcctatgct    660
cagattgtag tgactgtgct gagagttcct tctgggacca aagaaccaa  ggccttctcc    720
acatgctcct ctcacctggc tgtggtgtcc acgttctatg aacactcat  ggtattgtac    780
attgtgccct ctgctgttca ttctcagctc ctctccaagg tcattgccct gctctacaca    840
gtggtcactc ccatcttcaa ccctgtcatc tacaccttga ggaaccagga ggtgcagcag    900
gcactaagaa ggcttctcta ctgcaaacca actgaaatgt ga                        942
```

<210> SEQ ID NO 8
<211> LENGTH: 313
<212> TYPE: PRT
<213> ORGANISM: mouse

<400> SEQUENCE: 8

Met Gly Ile Leu Ser Thr Gly Asn Gln Thr Val Thr Glu Phe Val Leu
1               5                   10                  15

Leu Gly Phe His Glu Val Pro Gly Leu His Leu Leu Phe Phe Ser Val
            20                  25                  30

```
Phe Thr Ile Leu Tyr Ala Ser Ile Ile Thr Gly Asn Met Leu Ile Ala
             35                  40                  45
Val Val Val Ser Ser Gln Arg Leu His Thr Pro Met Tyr Phe Phe
 50                  55                  60
Leu Val Asn Leu Ser Phe Ile Glu Ile Val Tyr Thr Ser Thr Val Val
 65                  70                  75                  80
Pro Lys Met Leu Glu Gly Phe Leu Gln Glu Ala Thr Ile Ser Val Ala
                 85                  90                  95
Gly Cys Leu Leu Gln Phe Phe Val Phe Gly Ser Leu Ala Thr Asp Glu
                100                 105                 110
Cys Phe Leu Leu Ala Val Met Ala Tyr Asp Arg Tyr Leu Ala Ile Cys
             115                 120                 125
His Pro Leu Arg Tyr Pro His Leu Met Gly Pro Gln Trp Cys Leu Gly
         130                 135                 140
Leu Val Leu Thr Val Trp Leu Ser Gly Phe Met Val Asp Gly Leu Val
145                 150                 155                 160
Val Ala Leu Met Ala Gln Leu Arg Phe Cys Gly Pro Asn Leu Val Asp
                165                 170                 175
His Phe Tyr Cys Asp Phe Ser Pro Leu Met Val Leu Ala Cys Ser Asp
            180                 185                 190
Thr Gln Val Ala Gln Val Thr Thr Phe Val Leu Ser Val Val Phe Leu
        195                 200                 205
Thr Val Pro Phe Gly Leu Val Leu Ile Ser Tyr Ala Gln Ile Val Val
    210                 215                 220
Thr Val Leu Arg Val Pro Ser Gly Thr Arg Thr Lys Ala Phe Ser
225                 230                 235                 240
Thr Cys Ser Ser His Leu Ala Val Val Ser Thr Phe Tyr Gly Thr Leu
                245                 250                 255
Met Val Leu Tyr Ile Val Pro Ser Ala Val His Ser Gln Leu Leu Ser
            260                 265                 270
Lys Val Ile Ala Leu Leu Tyr Thr Val Val Thr Pro Ile Phe Asn Pro
        275                 280                 285
Val Ile Tyr Thr Leu Arg Asn Gln Glu Val Gln Gln Ala Leu Arg Arg
    290                 295                 300
Leu Leu Tyr Cys Lys Pro Thr Glu Met
305                 310

<210> SEQ ID NO 9
<211> LENGTH: 948
<212> TYPE: DNA
<213> ORGANISM: human

<400> SEQUENCE: 9
atggaaattg tctccacagg aaacgaaact attactgaat tgtcctcct tggcttctat      60 gacatccctg aactgcattt cttgttttt attgtattca ctgctgtcta tgtcttcatc     120
atcataggga atatgctgat tattgtagca gtggttagcc cccagaggct ccacaaaccc     180
atgtatattt tcttggcgaa tctgtccttc ctggatattc tctacacctc cgcagtgatg     240
ccaaaaatgc tggagggctt cctgcaagaa gcaactatcc tgtggctgg ttgcttgctc     300 cagttcttta tcttcggctc tctagccaca gctgaatgct actgctggc tgtcatggca     360 tatgaccgct acctggcaat tgctacccca ctccactacc cactcctgat ggggcccaga     420
cggtacatgg ggctggtggt cacaacctgg ctctctggat tgtgtggtaga tggactggtt     480 gtggccctgg tggcccagct gaggttctgt ggccccaacc acattgacca gttttactgt     540
```

```
gactttatgc ttttcgtggg cctggcttgc tcggatccca gagtggctca ggtgacaact    600
ctcattctgt ctgtgttctg cctcactatt ccttttggac tgattctgac atcttatgcc    660
agaattgtgg tggcagtgct gagagttcct gctggggcaa gcaggagaag ggctttctcc    720
acatgctcct cccacctagc tgtagtgacc acattctatg gaacgctcat gatctttat    780 gttgcaccct ctgctgtcca ttcccagctc ctctccaagg tcttctccct gctctacact    840
gtggtcaccc ctctcttcaa tcctgtgatc tataccatga ggaacaagga ggtgcatcag    900
gcacttcgga agattctctg tatcaaacaa actgaaacac ttgattga                 948
```

<210> SEQ ID NO 10
<211> LENGTH: 315
<212> TYPE: PRT
<213> ORGANISM: human

<400> SEQUENCE: 10

```
Met Glu Ile Val Ser Thr Gly Asn Glu Thr Ile Thr Glu Phe Val Leu
1               5                   10                  15

Leu Gly Phe Tyr Asp Ile Pro Glu Leu His Phe Leu Phe Phe Ile Val
            20                  25                  30

Phe Thr Ala Val Tyr Val Phe Ile Ile Gly Asn Met Leu Ile Ile
        35                  40                  45

Val Ala Val Val Ser Ser Gln Arg Leu His Lys Pro Met Tyr Ile Phe
    50                  55                  60

Leu Ala Asn Leu Ser Phe Leu Asp Ile Leu Tyr Thr Ser Ala Val Met
65              70                  75                  80

Pro Lys Met Leu Glu Gly Phe Leu Gln Glu Ala Thr Ile Ser Val Ala
                85                  90                  95

Gly Cys Leu Leu Gln Phe Phe Ile Phe Gly Ser Leu Ala Thr Ala Glu
            100                 105                 110

Cys Leu Leu Leu Ala Val Met Ala Tyr Asp Arg Tyr Leu Ala Ile Cys
        115                 120                 125

Tyr Pro Leu His Tyr Pro Leu Met Gly Pro Arg Arg Tyr Met Gly
    130                 135                 140

Leu Val Val Thr Thr Trp Leu Ser Gly Phe Val Asp Gly Leu Val
145             150                 155                 160

Val Ala Leu Val Ala Gln Leu Arg Phe Cys Gly Pro Asn His Ile Asp
                165                 170                 175

Gln Phe Tyr Cys Asp Phe Met Leu Phe Val Gly Leu Ala Cys Ser Asp
            180                 185                 190

Pro Arg Val Ala Gln Val Thr Thr Leu Ile Leu Ser Val Phe Cys Leu
        195                 200                 205

Thr Ile Pro Phe Gly Leu Ile Leu Thr Ser Tyr Ala Arg Ile Val Val
    210                 215                 220

Ala Val Leu Arg Val Pro Ala Gly Ala Ser Arg Arg Ala Phe Ser
225             230                 235                 240

Thr Cys Ser Ser His Leu Ala Val Val Thr Thr Phe Tyr Gly Thr Leu
                245                 250                 255

Met Ile Phe Tyr Val Ala Pro Ser Ala Val His Ser Gln Leu Leu Ser
            260                 265                 270

Lys Val Phe Ser Leu Leu Tyr Thr Val Thr Pro Leu Phe Asn Pro
        275                 280                 285

Val Ile Tyr Thr Met Arg Asn Lys Glu Val His Gln Ala Leu Arg Lys
    290                 295                 300
```

Ile Leu Cys Ile Lys Gln Thr Glu Thr Leu Asp
305                 310                 315

<210> SEQ ID NO 11
<211> LENGTH: 936
<212> TYPE: DNA
<213> ORGANISM: mouse

<400> SEQUENCE: 11

```
atgaaaacct tcagcagccc catcaactcc agcaccacca ctggcttcat tctcttgggc      60
ttcccctgcc ccagggaggg gcaaatcctc ctctttgtgc tcttctccat tgtctacctg     120
cttaccctca tgggcaacac ttgcatcatc tttgcagtat gctgggatca gagactccac     180
acacccatgt acctactgct ggccaacttc tccttcctgg agatctggta tgttacctcc     240
acagtcccca acatgttggc caatttcctc tctgacacca aggtcatctc tttctctgga     300
tgcttcctgc agttctattt cttcttctcc ttgggttcta cagaatgcct tttcctggca     360
gtcatggcat tgatcgata ccttgccatc tgtaggccac tacattatcc tgctctcatg     420
actgggagcc tctgcaacat ccttgtgatc agttgctggg tgcttggttt cctctggttc     480
cctgttccca tcatcatcat ctcccagatg tccttctgtg ggtccagaat tatagaccac     540
ttcctgtgtg acccaggccc tctattggcc ctcacctgtt ccagagcccc attaatggag     600
gttttctgga caattataac atctcttatc ctgttcgttc ctttcctctt catcatggga     660
tcttatacat tggtcctgag agctgtgttc agagttcctt caagagatgg acaaaaaaag     720
gctttctcca cttgcggatc tcatctcaca gtagttttac tcttttatgg ctcagtgatg     780
ataatgtatc taagcccgac ctctgagcat gaagctggaa tgcagaagct tgtgactcta     840
ttttattctg tggttactcc actcattaat cctgtgatat acagtctgag gaacaaggat     900
atgaaacatg ccctgcagaa gattttaaga acataa                               936
```

<210> SEQ ID NO 12
<211> LENGTH: 311
<212> TYPE: PRT
<213> ORGANISM: mouse

<400> SEQUENCE: 12

Met Lys Thr Phe Ser Ser Pro Ile Asn Ser Thr Thr Thr Gly Phe
1               5                   10                  15

Ile Leu Leu Gly Phe Pro Cys Pro Arg Glu Gly Gln Ile Leu Leu Phe
                20                  25                  30

Val Leu Phe Ser Ile Val Tyr Leu Leu Thr Leu Met Gly Asn Thr Cys
            35                  40                  45

Ile Ile Phe Ala Val Cys Trp Asp Gln Arg Leu His Thr Pro Met Tyr
        50                  55                  60

Leu Leu Leu Ala Asn Phe Ser Phe Leu Glu Ile Trp Tyr Val Thr Ser
65                  70                  75                  80

Thr Val Pro Asn Met Leu Ala Asn Phe Leu Ser Asp Thr Lys Val Ile
                85                  90                  95

Ser Phe Ser Gly Cys Phe Leu Gln Phe Tyr Phe Phe Phe Ser Leu Gly
            100                 105                 110

Ser Thr Glu Cys Leu Phe Leu Ala Val Met Ala Phe Asp Arg Tyr Leu
        115                 120                 125

Ala Ile Cys Arg Pro Leu His Tyr Pro Ala Leu Met Thr Gly Ser Leu
    130                 135                 140

```
Cys Asn Ile Leu Val Ile Ser Cys Trp Val Leu Gly Phe Leu Trp Phe
145                 150                 155                 160

Pro Val Pro Ile Ile Ile Ser Gln Met Ser Phe Cys Gly Ser Arg
            165                 170                 175

Ile Ile Asp His Phe Leu Cys Asp Pro Gly Pro Leu Leu Ala Leu Thr
                180                 185                 190

Cys Ser Arg Ala Pro Leu Met Glu Val Phe Trp Thr Ile Ile Thr Ser
            195                 200                 205

Leu Ile Leu Phe Val Pro Phe Leu Phe Ile Met Gly Ser Tyr Thr Leu
    210                 215                 220

Val Leu Arg Ala Val Phe Arg Val Pro Ser Arg Asp Gly Gln Lys Lys
225                 230                 235                 240

Ala Phe Ser Thr Cys Gly Ser His Leu Thr Val Val Leu Leu Phe Tyr
            245                 250                 255

Gly Ser Val Met Ile Met Tyr Leu Ser Pro Thr Ser Glu His Glu Ala
            260                 265                 270

Gly Met Gln Lys Leu Val Thr Leu Phe Tyr Ser Val Val Thr Pro Leu
            275                 280                 285

Ile Asn Pro Val Ile Tyr Ser Leu Arg Asn Lys Asp Met Lys His Ala
            290                 295                 300

Leu Gln Lys Ile Leu Arg Thr
305                 310

<210> SEQ ID NO 13
<211> LENGTH: 930
<212> TYPE: DNA
<213> ORGANISM: human

<400> SEQUENCE: 13
atgagggaaa ataaccagtc ctctacactg gaattcatcc tcctgggagt tactggtcag      60
caggaacagg aagatttctt ctacatcctc ttcttgttca tttacccccat cacattgatt    120 ggaaacctgc tcatcgtcct agccatttgc tctgatgttc gccttcacaa ccccatgtat    180
tttctccttg ccaacctctc cttggttgac atcttcttct catcggtaac catccctaag    240
atgctggcca accatctctt gggcagcaaa tccatctctt tgggggatg cctaacgcag     300 atgtatttca tgatagcctt gggtaacaca gacagctata ttttggctgc aatggcatat   360
gatcgagctg tggccatcag ccgcccactt cactacacaa caattatgag tccacggtct   420
tgtatctggc ttattgctgg gtcttgggtg attggaaatg ccaatgccct cccccacact   480
ctgctcacag ctagtctgtc cttctgtggc aaccaggaag tggccaactt ctactgtgac   540 attacccct tgctgaagtt atcctgttct gacatccact tcatgtgaa gatgatgtac    600 ctaggggttg gcatttctc tgtgccatta ctatgcatca ttgtctccta tattcgagtc   660
ttctccacag tcttccaggt tccttccacc aagggcgtgc tcaaggcctt ctccacctgt   720
ggttcccacc tcacggttgt ctctttgtat tatggtacag tcatgggcac gtatttccgc   780 ccttttgacca attatagcct aaaagacgca gtgatcactg taatgtacac ggcagtgacc   840
ccaatgttaa atcctttcat ctacagtctg agaaatcggg acatgaaggc tgccctgcgg   900
aaactcttca caagagaat ctcctcgtga                                        930

<210> SEQ ID NO 14
<211> LENGTH: 309
<212> TYPE: PRT
<213> ORGANISM: human
```

```
<400> SEQUENCE: 14

Met Arg Glu Asn Asn Gln Ser Ser Thr Leu Glu Phe Ile Leu Leu Gly
1               5                   10                  15

Val Thr Gly Gln Gln Glu Gln Glu Asp Phe Phe Tyr Ile Leu Phe Leu
            20                  25                  30

Phe Ile Tyr Pro Ile Thr Leu Ile Gly Asn Leu Leu Ile Val Leu Ala
            35                  40                  45

Ile Cys Ser Asp Val Arg Leu His Asn Pro Met Tyr Phe Leu Leu Ala
50                  55                  60

Asn Leu Ser Leu Val Asp Ile Phe Phe Ser Ser Val Thr Ile Pro Lys
65                  70                  75                  80

Met Leu Ala Asn His Leu Leu Gly Ser Lys Ser Ile Ser Phe Gly Gly
                85                  90                  95

Cys Leu Thr Gln Met Tyr Phe Met Ile Ala Leu Gly Asn Thr Asp Ser
            100                 105                 110

Tyr Ile Leu Ala Ala Met Ala Tyr Asp Arg Ala Val Ala Ile Ser Arg
            115                 120                 125

Pro Leu His Tyr Thr Thr Ile Met Ser Pro Arg Ser Cys Ile Trp Leu
130                 135                 140

Ile Ala Gly Ser Trp Val Ile Gly Asn Ala Asn Ala Leu Pro His Thr
145                 150                 155                 160

Leu Leu Thr Ala Ser Leu Ser Phe Cys Gly Asn Gln Glu Val Ala Asn
                165                 170                 175

Phe Tyr Cys Asp Ile Thr Pro Leu Leu Lys Leu Ser Cys Ser Asp Ile
            180                 185                 190

His Phe His Val Lys Met Met Tyr Leu Gly Val Gly Ile Phe Ser Val
            195                 200                 205

Pro Leu Leu Cys Ile Ile Val Ser Tyr Ile Arg Val Phe Ser Thr Val
            210                 215                 220

Phe Gln Val Pro Ser Thr Lys Gly Val Leu Lys Ala Phe Ser Thr Cys
225                 230                 235                 240

Gly Ser His Leu Thr Val Val Ser Leu Tyr Tyr Gly Thr Val Met Gly
                245                 250                 255

Thr Tyr Phe Arg Pro Leu Thr Asn Tyr Ser Leu Lys Asp Ala Val Ile
            260                 265                 270

Thr Val Met Tyr Thr Ala Val Thr Pro Met Leu Asn Pro Phe Ile Tyr
            275                 280                 285

Ser Leu Arg Asn Arg Asp Met Lys Ala Ala Leu Arg Lys Leu Phe Asn
290                 295                 300

Lys Arg Ile Ser Ser
305

<210> SEQ ID NO 15
<211> LENGTH: 24
<212> TYPE: DNA
<213> ORGANISM: artificial
<220> FEATURE:
<223> OTHER INFORMATION: Flag tag

<400> SEQUENCE: 15
gattacaagg acgacgacga taag                                    24

<210> SEQ ID NO 16
<211> LENGTH: 8
<212> TYPE: PRT
<213> ORGANISM: artificial
```

```
<220> FEATURE:
<223> OTHER INFORMATION: Flag tag

<400> SEQUENCE: 16

Asp Tyr Lys Asp Asp Asp Asp Lys
1               5

<210> SEQ ID NO 17
<211> LENGTH: 60
<212> TYPE: DNA
<213> ORGANISM: artificial
<220> FEATURE:
<223> OTHER INFORMATION: Rho tag

<400> SEQUENCE: 17
atgaacggga ccgagggccc aaacttctac gtgcctttct ccaacaagac gggcgtggtg    60

<210> SEQ ID NO 18
<211> LENGTH: 20
<212> TYPE: PRT
<213> ORGANISM: artificial
<220> FEATURE:
<223> OTHER INFORMATION: Rho tag

<400> SEQUENCE: 18

Met Asn Gly Thr Glu Gly Pro Asn Phe Tyr Val Pro Phe Ser Asn Lys
1               5                   10                  15

Thr Gly Val Val
            20

<210> SEQ ID NO 19
<211> LENGTH: 51
<212> TYPE: DNA
<213> ORGANISM: artificial
<220> FEATURE:
<223> OTHER INFORMATION: Lucy tag

<400> SEQUENCE: 19
atgagacccc agatcctgct gctcctggcc ctgctgaccc taggcctggc t              51

<210> SEQ ID NO 20
<211> LENGTH: 17
<212> TYPE: PRT
<213> ORGANISM: artificial
<220> FEATURE:
<223> OTHER INFORMATION: Lucy tag

<400> SEQUENCE: 20

Met Arg Pro Gln Ile Leu Leu Leu Ala Leu Leu Thr Leu Gly Leu
1               5                   10                  15

Ala
```

CELL LINES FOR SCREENING ODORANT AND AROMA RECEPTORS

RELATED APPLICATIONS

This application is a national stage application under 35 U.S.C. § 371 filing of International Patent Application PCT/US2016/036777, filed Jun. 9, 2016, which claims the benefit of U.S. Provisional Application No. 62/173,762, filed Jun. 10, 2015 and U.S. Provisional Application No. 62/221,580 filed Sep. 21, 2015.

FIELD

The technical field is directed to odorant and aroma receptors and assays that can be used to identify odorant and/or aroma compounds or modulators of such. The assays are more specifically directed to engineered cell lines that exhibit improved odorant receptor activity.

BACKGROUND

Odors are initially encoded in the peripheral olfactory system (i.e. the nose) through interactions between volatile flavor and fragrance compounds and odorant receptor (OR) proteins that reside on the membranes of olfactory receptor neurons of olfactory epithelia tissue. Such interactions occur in an odorant-specific combinatorial manner where any single OR may be activated by multiple odorants, and conversely most odorants are capable of activating several different ORs. For a given odorant/aroma compound, or mixture, these receptor interactions generate neurophysiological signals in the brain and ultimately give rise to conscious odor perception. Approximately ~400 ORs genes in the human genome can be activated by thousands or more odorant stimuli and it is the inherent complexity of the combinatorial interactions between odorants and receptors that allows for the breadth of olfactory sensations we can perceive. Elucidating the these interactions can lead to the discovery of beneficial products including, but not limited to, malodor counteractants that block the perception of unpleasant odors, new flavor and fragrance ingredients that replace non-biodegradable or toxic compounds, and odor enhancers that would limit our reliance on difficult to source compounds from natural sources.

There is a need for example, but not limited to, new methods that can functionally express ORs on the cell surface for reliable decoding of the OR codes. There is a further need for a method that functionally expresses the ORs in non-olfactory cells (for example, but not limited to, heterologous cell lines) that are amenable to high-throughput screens with libraries of volatile flavor and fragrance compounds for comprehensive characterization of OR activity. This could significantly expedite the discovery of highly desirable malodour counteractants, odor modulators, and new flavor or fragrance compounds.

Certain proteins derived from olfactory sensory neurons can improve cell surface localization of odorant receptors in non-olfactory cell lines. These proteins function by assisting in the trafficking of the odorant receptors from the endoplasmic reticulum to the Golgi apparatus and plasma membrane of the cell. Receptor-Transporting Protein 1 (RTP1), Receptor-Transporting Protein 2 (RTP2), and Receptor Expression Enhancing Protein 1 (REEP1) have been reported to improve odorant receptor plasma membrane localization and therefore function in non-olfactory cells. RTP1 has been reported to be the most effective odorant receptor chaperone. This protein has been shown to act, in part, by interacting with odorant receptors in the endoplasmic reticulum. A non-olfactory cell line that is amenable to high-throughput screening and that contains the RTP1 gene is therefore highly desirable for comprehensive decoding of the combinatorial interactions between odorants and odorant receptors.

Even more desirable is a cell line that consistently produces the RTP1 protein, including but not limited to RTP1S, by stably expressing the gene from the endogenous RTP1 gene locus. However, current techniques for developing cell lines that stably expresses the endogenous RTP1 gene involve inefficient and cumbersome molecular biology approaches for the insertion of DNA into cultured cells that otherwise do not express the gene. Hence it is desirable to use a technique that avoids such approaches to develop a stable cell line and that allows for the consistent expression of the endogenous RTP1 without the need to use recombinant methods.

CRISPR/Cas9 is a highly efficient genome editing tool used to generate precise genome modifications such as insertions and deletions. For example, a particular use of CRISPR/Cas9 enables the expression of a gene that may be otherwise silent in a cell line. By incorporating a transcriptional promoter upstream of the gene, a cell line may then express an endogenous gene that is otherwise inactive.

SUMMARY

A cell comprising an activated endogenous RTP1 gene within the cell wherein the cell further expresses a RTP1 protein.

Provided herein is a non-olfactory cell line with improved odorant receptor function comprising an activated endogenous RTP1 gene.

Provided herein is a non-olfactory cell line comprising an activated endogenous RTP1 gene within the cell which further expresses an RTP1 protein.

Further provided herein is a method for activating an endogenous RTP1 gene in a eukaryotic cell comprising:
 a. introducing a guide RNA complementary to a genomic target site upstream of the RTP1 gene;
 b. introducing a Cas nuclease protein to make a complex with the guide RNA; and
 c. using the guide RNA/Cas9 genome targeting complex to deliver the gene activating elements for the RTP1 gene specifically.

Also provided herein is a method for identifying a compound that activates, mimics, blocks, inhibits, modulates, and/or enhances the activity of an olfactory receptor in a non-olfactory cell wherein the cell comprises an activated endogenous RTP1 gene wherein the method further comprises:
 a. contacting the receptor, or a chimera or fragment thereof with a compound that activates, mimics, blocks, inhibit, modulates and/or enhances the receptor and
 b. determining whether the compound has an effect on the activity of the receptor.

DETAILED DESCRIPTION

Figure 1:
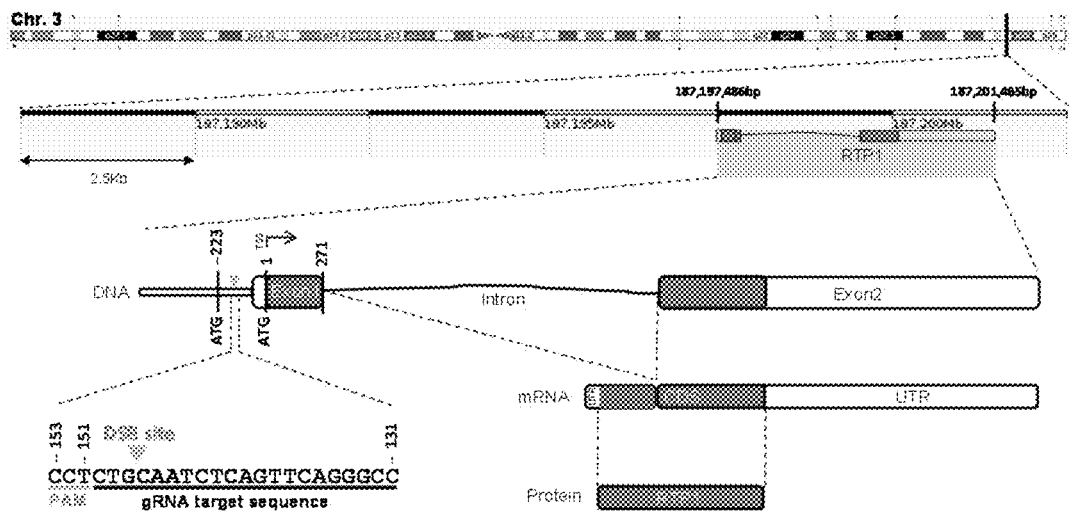
FIG. 1 shows a schematic of the endogenous RTP1 gene locus and the specific target site used for genome editing.

For the descriptions herein and the appended claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

In one embodiment, a cell is provided comprising a nucleic acid encoding an odorant receptor.

In a further embodiment, the cell is provided comprising a nucleic acid encoding an odorant receptor selected from the group consisting of Olfr741, Olfr742, Olfr96, Olfr740, OR1A1, and OR11A1.

In yet a further embodiment, the cell is provided herein comprises a constitutive promoter upstream of an endogenous RTP1 gene locus such that the promoter drives the expression of the endogenous RTP1 gene.

In mouse olfactory sensory neurons, the RTP1 transcript contains two alternative translational start sites that can lead to two distinct forms of the RTP1 protein: a long version (RTP1L) and a short version (RTP1S). However, it is the RTP protein that is predominantly expressed in the mouse olfactory neurons. Also, non-olfactory cells (for example, but not limited to, HEK293T) heterologously expressing the full RTP1 coding sequence predominantly express RTP1L even though the RTP1S coding sequence is contained within RTP1L. However, RTP1S is preferred for odorant receptor screening in non-olfactory cells since it is known that RTP1S strongly outperforms RTP1L with respect to cell surface OR expression. We have surprisingly found that endogenous activation of the full RTP1 gene leads preferentially to the expression of RTP1S.

In a further embodiment, a cell is provided herein that comprises a constitutive promoter upstream of an endogenous RTP1 gene locus that drives the expression of the short version of RTP1 gene, RTP1S.

Provided herein is a non-olfactory cell line comprising an activated endogenous RTP1 gene within the cell which further expresses the short version of an RTP1 protein, RTP1S.

In yet a further embodiment, the constitutive promoter is selected from the group consisting of CMV, PGK, EF1a and SV40.

In one embodiment, the promoter is CMV, originating from the Cytomegalovirus.

In one embodiment, a cell provided herein comprises an inducible promoter upstream of an endogenous RTP1 gene locus such that the promoter drives the expression of the RTP1 gene when the corresponding operator is present.

In a further embodiment, the inducible promoter is a Tetracycline Response Element (TRE) promoter inducible by administration of tetracycline (or its analogue doxycycline).

In one embodiment, the Cas nuclease protein is a Cas9 protein.

In a further embodiment, the Cas9 protein is selected from the group consisting of Cas9, dCAs9 (deactivated Cas9) and Cas9 nickase.

In one embodiment, the guide RNA (gRNA) sequence may be designed based on state-of-the-art rules (Doench et al., Nat Biotech (2014)) and publicly available guide RNA design tools for efficient genomic targeting (e.g. wwws.blueheronbio.com/external/tools/gRNASrc.jsp). The homologous arms may be used that are 800 bp long on each side of the specific Cas9 generated double strand DNA break. It is useful to carefully review the integration site of the CMV promoter to avoid unwanted translational start site before the endogenous RTP1 start site.

Preferably the original cell line used for CRISPR/Cas9 engineering should be from a mammalian origin and carry the RTP1 gene locus. Such cell lines include, but are not restricted to, HEK293, HEK293T, HeLa, CHO, OP6, HeLa-S3, HEKn, HEKa, PC-3, Calu1, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, BHK, BHK-21, BR 293, BxPC3, C3H-10T1/2, C6/36, Cal-27, CHO-7, CHO-IR, CHO-K1, CHO-K2, CHO-T, CHO Dhfr−/−, COS-7, HL-60, LNCap, MCF-7, MCF-10A, MDCK II, SkBr3, Vero cells, immortalized olfactory cells, immortalized taste cells, and transgenic varieties thereof. Cell lines are available from a variety of sources known to those with skill in the art (see, e.g., the American Type Culture Collection (Manassas, Va.).

Hence, in some embodiments a stable cell line is selected from the group consisting of HEK293, HEK293T, HeLa, CHO, OP6, HeLa-S3, HEKn, HEKa, PC-3, Calu1, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, BHK, BHK-21, BR 293, BxPC3, C3H-10T1/2, C6/36, Cal-27, CHO-7, CHO-IR, CHO-K1, CHO-K2, CHO-T, CHO Dhfr−/−, COS-7, HL-60, LNCap, MCF-7, MCF-10A, MDCK II, SkBr3, Vero cells, immortalized olfactory cells, immortalized taste cells, and transgenic varieties thereof.

In yet a further embodiment, the complex allows for the cleavage of the target nucleic acid sequence adjacent to the guide RNA sequence and Cas9 protein complex delivered to the cell and wherein the method further comprises introducing a donor DNA comprising a CMV promoter into the cell.

In one embodiment, the guide RNA sequence and Cas9 protein complex allows for the cleavage of the target nucleic acid sequence adjacent to the guide RNA sequence and Cas9 protein complex and wherein the method further comprises introducing a donor DNA comprising a CMV promoter through cellular homology directed repair mechanism at the cleavage site.

In a further embodiment is a cell line modified to stably express the endogenous RTP1 gene under the CMV promoter.

In a further embodiment a donor DNA may also comprise an antibiotic selection cassette (e.g., containing the puromycin resistance gene). Cultivating cells in antibiotic containing culture media after DNA delivery can be beneficial as it eliminates cells that did not undergo proper DNA integration and thus allows one to efficiently select recombined clonal cell populations that acquired a resistance marker hence the desired integration of the donor DNA (e.g. the constitutive promoter CMV). Such antibiotic resistance gene can subsequently be removed by engineering it with flanking "frt" sites that are specifically recognized by the Flippase enzyme. This cassette is then removed by delivering said enzyme to the cells.

In one embodiment the complex works by targeting specific locations in the genome and further recruiting transcription factors that activate downstream endogenous genes such as RTP1 without the need for cleaving the DNA. This is done by fusing the Cas9 protein to a transcription activation domain to form a complex wherein the complex is not capable of cleaving the target nucleic acid sequence. The method provides guide RNA directed DNA targeting (i.e. upstream of the RTP1 gene) of the Cas9 fused transcription activation domain. Instead of cleaving the DNA to allow for a promoter integration, it transiently binds and recruits transcription factors that activate the gene without the need for engineering or modifying the genome that is, the d. This may be done through the use of a deactivated version of Cas9 called dCas9, fused to specific transcription factor recruiting elements such as VP64, VPR and SAM, or through the use of a modified guide RNA (e.g. a truncated guide RNA). This fusion protein does not cleave the nucleic acid.

In one embodiment provided herein is a method comprising introducing a nucleic acid encoding an olfactory receptor into the cell.

In a further embodiment provided herein is a method for identifying a compound that activates, mimics, blocks, inhibits, modulates, and/or enhances the activity of an olfactory receptor in a non-olfactory cell wherein the cell comprises an activated endogenous RTP1 gene wherein the method further comprises:
 a. contacting the receptor, or a chimera or fragment thereof with a compound that activates, mimics, blocks, inhibit, modulates and/or enhances the receptor and
 b. determining whether the compound has an effect on the activity of the receptor.

In one embodiment, the olfactory receptor is from the group consisting of a musk and a malodor receptor.

In a particular embodiment, the malodor receptor is selected from a skatole or indole receptor.

In a particular embodiment the musk receptor is selected from a polycyclic musk and a nitromusk receptor.

In one embodiment nucleic acids encoding an odorant receptor is introduced in the substantial absence of a $G_{olf}$ protein.

In one embodiment, the follow steps are carried out:
1. editing a cell line genome using CRISPR/Cas9 technology, including: (1) designing a DNA encoding a 'guide RNA' specific to the desired genomic DNA integration site located near the endogenous RTP1 genomic locus; and (2) a 'donor DNA' to be integrated into the genomic locus that comprises a constitutively active transcriptional promoter;
2. introducing the DNAs engineered in step 1 into a mammalian cell line;
3. selecting a cell line that has integrated the donor DNA into the desired genomic locus and that produces RTP1 mRNA via activation of the endogenous RTP1 gene.
4. introducing an odorant receptor DNA sequence into the selected cell line.
5. contacting a receptor, or chimera or fragment with a compound and assay whether the compound has an effect on the activity of the odorant receptor.

The methods provided herein allow for the use of cell lines to discover ingredients such as odor enhancers and blockers for cosmetic and industrial use (e.g. perfumes, perfumer enhancers, flavour enhancers, home and body deodorants). New ingredients may provide more favourable fragrant, toxicity and biodegradation profiles and/or exhibit greater potency.

Accordingly, a compound or mixture of compounds that that activate, mimic, block, inhibit, modulate, and/or enhance the activity of an olfactory receptor in a non-odorant cell obtained by any one of the methods disclosed herein.

In one embodiment, enhanced functional odorant receptor expression in heterologous expression systems is provided using CRISPR/Cas9 to specifically and constitutively activate the RTP1 gene which is silent (inactive) in regular HEK293T cells.

Definitions

The following terms have the meanings ascribed to them unless specified otherwise.

"Endogenous gene" refers to a gene that originates from within an organism, tissue, or cell.

The phrase "functional effects" includes the determination of any parameter that is indirectly or directly under the influence of the receptor, e.g., functional, physical and chemical effects. It includes, but not limited to, ligand binding, changes in ion flux, membrane potential, current flow, transcription, G protein binding, GPCR phosphorylation or dephosphorylation, signal transduction receptor-ligand interactions, second messenger concentrations (e.g., cAMP, cGMP IP3, or intracellular $Ca^{2+}$), in vitro, in vivo, and ex vivo and also includes other physiologic effects such increases or decreases of neurotransmitter or hormone release.

The phrase "determining whether the compound has an effect on the activity" in the context of assays is meant assays for a compound that increases or decreases a parameter that is indirectly or directly under the influence of an OR family member, e.g., functional, physical and chemical effects. Such functional effects can be measured by any means known to those skilled in the art, e.g., but not limited to, changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte OR gene expression; tissue culture cell OR expression; transcriptional activation of OR genes; ligand-binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

The term "expression vector" refers to any recombinant expression system for the purpose of expressing a nucleic acid sequence of the invention in vitro or in vivo, constitutively or inducibly, in any cell, including prokaryotic, yeast, fungal, plan insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

By "host cell" is meant a cell that contains an expression vector and supports the replication or expression of the expression vector. Host cells may be prokaryotic cells such as E. coli, or eukaryotic cells such as yeast, insect, amphibian, or mammalian cells such as CHO, HeLa, HEK-293, and the like, e.g., cultured cells, explants, and cells in vivo.

"Inhibitors," "activators," "counteractants" and "modulators" of OR genes or proteins are used interchangeably to refer to inhibitory, activating, or modulating molecules identified using in vivo, in vitro and in vivo assays for olfactory transduction, e.g., ligands, agonists, antagonists, enhancers, and their homologs and mimetics. Inhibitors are compounds that, e.g., bind to, partially or totally block stimulation, decrease, prevent, delay activation, inactivate, desensitize, or down regulate olfactory transduction, e.g., antagonists. Activators are compounds that, e.g., bind to, stimulate, increase, open activate, facilitate, enhance activation, sensitize, or up regulate olfactory transduction, e.g., agonists. Modulators include compounds that, e.g., alter the interaction of a receptor with: extracellular proteins that bind activators or inhibitor (e.g., odorant-binding proteins and other members of the hydrophobic carrier family); G proteins; kinases (e.g., homologs of rhodopsin kinase and beta adrenergic receptor kinases that are involved in deactivation and desensitization of a receptor); and arrestins, which also deactivate and desensitize receptors. Modulators can include genetically modified versions of OR family members, e.g., with altered activity, as well as naturally occurring and synthetic ligands, antagonists, agonists, small chemical molecules and the like. Such assays for inhibitors and activators include, e.g., expressing OR family members in cells or cell membranes, applying putative modulator compounds, in the presence or absence of flavor or fragrance molecules, e.g. Musks or malodors, and then determining the functional effects on olfactory transduction, as described above. Samples or assays comprising OR family members that are treated with a potential activator, inhibitor, or modulator are compared to control samples without the inhibitor, activator, or modulator to examine the extent of modulation.

The "N terminal domain" region starts at the N-terminus and extends to a region close to the start of the first transmembrane region. "Transmembrane domain," which comprises the seven "transmembrane regions," refers to the domain of OR polypeptides that lies within the plasma membrane, and may also include the corresponding cytoplasmic (intracellular) and extracellular loops. The seven transmembrane regions and extracellular and cytoplasmic loops can be identified using standard methods, as described in Kyte & Doolittle, J. Mol. Biol., 157:105-32 (1982), or in Stryer. The general secondary and tertiary structure of transmembrane domains, in particular the seven transmembrane domains of G protein-coupled receptors such as olfactory receptors, are known in the art. Thus, primary structure sequence can be designed or predicted based on known transmembrane domain sequences, as described in detail below. These transmembrane domains are useful for in vitro ligand-binding assays, both soluble and solid phase.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues.

Odorant Receptor or "OR" refers to one or more members of a family of G protein-coupled receptors that are expressed in olfactory cells. Olfactory receptor cells can also be identified on the basis of morphology or by the expression of proteins specifically expressed in olfactory cells. OR family members may have the ability to act as receptors for olfactory transduction.

Odorant Receptor or "OR" nucleic acids encode a family of G-protein coupled receptors with seven transmembrane regions that have "G protein-coupled receptor activity," e.g., they may bind to G proteins in response to extracellular stimuli and promote production of second messengers such as IP3, cAMP, cGMP, and $Ca^{2+}$ via stimulation of enzymes such as phospholipase C and adenylate cyclase.

"OR" polypeptides are considered as such if they pertain to the 7-transmembrane-domain G protein-coupled receptor superfamily encoded by a single ~1 kb long exon and exhibit characteristic olfactory receptor-specific amino acid motifs. The predicted seven domains are called "transmembrane" or "TM" domains TM I to TM VII connected by three predicted "internal cellular loop" or "IC" domains IC I to IC III, and three predicted "external cellular loop" or "EC" domains EC I to EC III. The motifs are defined as, but not restricted to, the MAYDRYVAIC motif overlapping TM III and IC II, the FSTCSSH motif overlapping IC III and TM VI, the PMLNPFIY motif in TM VII as well as three conserved C residues in EC II, and the presence of highly conserved GN residues in TM I [Zhang and Firestein (2002), The Olfactory Receptor Gene Superfamily of the Mouse. Nature Neuroscience: 5(2):124-33; Malnic et al., The Human Olfactory Receptor Gene Family: PNAS: 101(8):2584-9].

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

Nucleic acid and amino acid sequences identified and/or used herein are listed below:

```
Guide RNA target sequence (SEQ ID NO: 1 DNA)
                                       SEQ ID NO: 1
ctgcaatctcagttcagggcc Donor DNA for homology directed repair (SEQ ID NO:
2 DNA)
                                       SEQ ID NO: 2
ggggttttatggaagagtcttacttctcttttctttcatctatattttgt atttttctagaataaacccatatgatttttttaaaaggaaaaataattta ttaaaaatagcagcagaggcatgtatagtaaaggctgttttgcctgtggg tggtgctcctcttctgcgcttctataatcagcttggaaataatcttgtct gctcctgcctggctgatgcaatgctcctacctttgtgcacaggtggctgt tcttgcacaaggccattgcagcatggatcctattgcacagttattcagta cacagtcagctacaagcactgacatagagcttggcacatgtctgcaaacc ctacccacatgctcggatatgtttgaaatgaatgaattaatgaaccggtc tggggtcaacagcttgaatttgtatacaggctccgccatttataggctag gtgagtcctaggctcctgatctgtactgcagcaatagtaatcataactta agagacctccaattgtgttttgaaaatggcaaagtgctggtcacaagatg gctggggaagccgagagagagtttattattattgctccatctactaacaa atttacatctccccatccctcatttctccttggctgcctaaggcatcatg gttaccgtagcagccagatgctgatgatgcctccaggggacggcaaggtg aaactgagccagttcccagtcctcacctcccatactctttccaggccag ggtgagatggtctgaagctcagtctctggtcaggtccccactctgtctt ggatcatttagacccgcggccgcggcgcgcctcggaattcgattgaagtt cctattccgaagttcctattctctagaaagtataggaacttcggtgtgga aagtccccaggctccccagcaggcagaagtatgcaaagcatgcatctcaa ttagtcagcaaccatagtcccgcccctaactccgcccatcccgcccctaa ctccgcccagttccgccattctccgcccatggctgactaattttttttt atttatgcagaggccgaggccgcctcggcctctgagctattccagaagta gtgaggaggcttttttggaggcctaggcttttgcaaaaagcttgcatgcc tgcaggtcggccgccacgaccggtgccgccaccatcccctgacccacgcc cctgaccccctcacaaggagacgaccttccatgaccgagtacaagcccacg gtgcgcctcgccacccgcgacgacgtcccccgggccgtacgcaccctcgc cgccgcgttcgccgactacccgccacgcgccacaccgtcgacccggacc gccacatcgagcgggtcaccgagctgcaagaactcttcctcacgcgcgtc gggctcgacatcggcaaggtgtgggtcgcggacgacggcgccgcggtggc ggtctggaccacgccggagagcgtcgaagcgggggcggtgttcgccgaga tcggcccgcgcatggccgagttgagcggttcccggctggccgcgcagcaa cagatggaaggcctcctggcgccgcaccggcccaaggagcccgcgtggtt cctggccaccgtcggcgtctcgcccgaccaccagggcaagggtctgggca gcgccgtcgtgctccccggagtggaggcggccgagcgcgccggggtgccc gccttcctggagacctccgcgcccgcaacctccccttctacgagcggct cggcttcaccgtcaccgccgacgtcgaggtgcccgaaggaccgcgcacct ggtgcatgacccgcaagcccggtgcctgacgcccgccccacgacccgcag cgcccgaccgaaaggagcgcacgacccatggctccgaccgaagccaccc ggggcggcccgccgaccccgcacccgccccgagccccaccgactctag aggatcataatcagccataccacatttgtagaggttttacttgctttaaa aaacctcccacacctcccctgaacctgaaacataaaatgaatgcaattg ttgttgttaacttgtttattgcagcttataatggttacaaataaagcaat agcatcacaaatttcacaaataaagcatttttttcactgcgaagttccta ttccgaagttcctattctctagaaagtataggaacttcaatcactagtga attcacgcgttgacattgattattgactagttattaatagtaatcaatta cggggtcattagttcatagcccatatatggagttccgcgttacataactt acggtaaatggcccgcctggctgaccgcccaacgacccccgcccattgac gtcaataatgacgtatgttcccatagtaacgccaatagggactttccatt gacgtcaatgggtggagtatttacggtaaactgcccacttggcagtacat caagtgtatcatatgccaagtacgccccctattgacgtcaatgacggtaa atggcccgcctggcattatgcccagtacatgaccttatgggactttccta cttggcagtacatctacgtattagtcatcgctattaccatggtgatgcgg ttttggcagtacatcaatgggcgtggatagcggtttgactcacggggatt tccaagtctccacccattgacgtcaatgggagtttgttttggcaccaaa atcaacgggactttccaaaatgtcgtaacaactccgccccattgacgcaa atgggcggtaggcgtgtacggtgggaggtctatataagcagagctcgttt agtgaaccgtgtttaaacctcttcagagactccctcctccccaagctctg tcttctggcaacctgcctggttgccgtggaaacaggttccactgcggaca
```

-continued aaggagggagctgggtcctgcttcctcctggtcttgtcgatgaggatttt
tagaccgtggagactgcgctgccctgccctgcacctaccctcactctccg
tgttctcactaaggtggaaattgccttccctcactactgacgagaccatg
tgtaaaagcgtgaccacagatgagtggaagaaagtcttctatgagaagat
ggaggaggcaaagccggctgacagctgggacctcatcatagaccccaacc
tcaagcacaatgtgctgagccctggttggaagcagtacctggaattgcat
gcttcaggcaggtgagtagcccaggaaagtggatcccgcaggccgcctc
taggtccctagctctggggcaccttccaaggagaggaagattacgtagaa
cccaagtgtttagcttcaatctcactattaggctggcgtagactggaagt
cagagaaagagtccctaactgggaactacgacacttgagttggatttcag
ctcttctactgatcacctgtgttactcttcctctctgagtcacaattttt
ccgtctggaaaataaagacatagaatatacgtatgagtcctacacactga
catttacatattttctattttaacagtctcttaaaaagtagtttaaaac
cagagaagaagggtttgaggcccactgggggtcgagacgtccgtgctctg
gtcctgggaccggtttaaatctatttaa Mouse Olfr741 (SEQ ID NO: 3 DNA; SEQ ID NO: 4 PROTEIN)

SEQ ID NO: 3
atgaaaaccctcagcagccccagcaactccagcaccatcactggcttcat
cctcttgggcttcgcctacccagggaggggcaaattctcctctttgtga
tcttcttcattgtttacatactcattcttatgggcaacgcttccatcatc
tgtgctgtgtactgtgatcagagactccacacccccatgtaccttctgct
ggccaacttctccttcatggagattggatatgtcacctccacagtcccca
acatgttggccaacttcctttcagacaccaaggtcatctctttctctgga
tgcttcctgcagttctatttcttcttctcctttggttctacagaatgctt
tttcctggcagtcatggcatttgatcgataccttgccatctgtaggccac
tacattatccttctctcatgactgggcgcctccgaaacaccttgtgacc
agttgctgggtgcttggtttcctctggttccctgtacccatcatcatcat
ctcccagatgtccttctgtgggtccagaattatagaccacttcctgtgtg
acccaggccctcttttggcccttgcctgttccagagtcccattgatagag
gttttctggtccattataatgtctatgctcctggttattccttcctctt
catcatgggaacttacatattggtcctaagagctgtgtttagacttcctt
caagagaaggacaaaaaaggcttctccacttgcgggtctcatctcaca
gtagtttcactcttttattgctcagtgatgataatgtatctgagcccaac
atctgagcatgaggccggaatgcagaagcttgtaactctattttattctg
tgggtacaccactgcttaatcctgtgatatacagtctgaggaacaaagat
atgaaaaatgccctacagaagattttga SEQ ID NO: 4
mktlsspsnsstitgfillgfaypreggqillfyiffivyililmgnasii
cavycdqrlhtpmyllanfsfmeigyvtstvpnmlanflsdtkvisfsg
cflqfyfffsfgstecfflavmafdrylaicrplhypslmtgrlrntlvt
scwvlgflwfpvpiiiisqmsfcgsriidhflcdpgpllalacsrvplie
vfwsiimsmllvipflfimgtyilvlravfrlpsreggkkafstcgshlt vvslfycsvmimylsptseheagmqklvtlfysvgtpllnpmiyslrnkd
mknalqkilrt Mouse Olfr742 (SEQ ID NO: 5 DNA; SEQ ID NO: 6 PROTEIN)

SEQ ID NO: 5
atgaaaaccctcagcagccccagcaactccagcaccatcactggcttcat
cctcttgggcttccctgccccagggaggggcaaatcctcctctttgtga
ccttcttcattgtttacatactcattcttatgggcaatgcttccatcatc
tgtgctgtgtactgtgatcagagcctccacacccccatgtacttcctgct
ggccaacttctccttcctggagatctggtatgtcacctccacagtcccca
acatgttggccaacttcctttcagacaccaaggtcatctctttctctgga
tgcttcctgcagttctatttcttcttctcctttggttctacagaatgctt
tttcctggcagtcatggcatttgatcgataccttgccatctgtaggccac
tacattatccttctctcatgactgggcacctctgcaacatccttgtgatc
agttgctgggtgcttggtttcctctggttccctgtacccatcatcatcat
ctcccagatgtccttctgtgggtccagaattatagaccacttcctgtgtg
acccaggccctcttttggcccttgcctgttccagagcccattgatggag
gttttctggacaattataatgtctatgctcctggttattccttcctctt
catcatgggaacttacatattggtcctaagagctgtgtttagacttcctt
caagagatggacaaaaaaaggccttctccacttgcgggtctcatctcaca
gtagtttcactcttttattgctcagtgatgaaaatgtatttgagcccaac
atctgagcatgaagctggaatgcagaagcttgtaactctattttattctg
tgggtactccactacttaatcctgtgatatacagtctgaggaacaaagat
atgaaaaatgccctgcagaagattttaagaacataa SEQ ID NO: 6
mktlsspsnsstitgfillgfpcpreggqillfvtffivyililmgnasii
cavycdqslhtpmyfllanfsfleiwyvtstvpnmlanflsdtkvisfsg
cflqfyfffsfgstecfflaymafdrylaicrplhypslmtghlcnilvi
scwvlgflwfpvpiiiisqmsfcgsriidhflcdpgpllalacsraplme
vfwtiimsmllvipflfimgtyilvlravfrlpsrdgqkkafstcgshlt
vvslfycsvmkmylsptseheagmqklvtlfysvgtpllnpviyslrnkd
mknalqkilrt Mouse Olfr96 (SEQ ID NO: 7 DNA; SEQ ID NO: 8 PROTEIN)

SEQ ID NO: 7
atgggaatcctttccacaggaaatcaaactgtcactgagtttgtacttct
tggtttccatgaagtccctgggctgcacctcctgttttttttctgtgttca
ccatcctctatgcctccatcatcacagggaacatgctcattgcagtggtg
gtggtgagctcccagaggcttcacacacccatgtatttctttctggtgaa
tctgtccttcatagagattgtctatacctccacagtggtgcccaaaatgc
tggaaggcttcttacaggaggccaccatatctgtggctggctgcttgctc
cagtcttttgtttttggctctctggccacagatgagtgttttctgctggc
tgtgatggcatatgatcgatatctcgcaatttgtcaccctctacgatacc
cacacctcatggggcctcaatggtgcctggggttggtgctcacagtctgg

```
ctgtctggcttcatggtagatggactagttgttgctctgatggcccagtt
gagattctgtggccccaacttagttgatcacttttactgtgattttcac
ctttgatggtcctggcttgctcagataccaagtggcccaggtgactaca
tttgttctctctgtggtcttcctgactgtcccctttgggctggttctgat
ctcctatgctcagattgtagtgactgtgctgagagttccttctgggacca
gaagaaccaaggccttctccacatgctcctctcacctggctgtggtgtcc
acgttctatggaacactcatggtattgtacattgtgccctctgctgttca
ttctcagctcctctccaaggtcattgccctgctctacacagtggtcactc
ccatcttcaaccctgtcatctacaccttgaggaaccaggaggtgcagcag
gcactaagaaggcttctctactgcaaaccaactgaaatgtga
```

SEQ ID NO: 8
```
Mgilstgnqtvtefvllgfhevpglhllffsvftilyasiitgnmliavv
vvssqrlhtpmyfflvnlsfieivytstvvpkmlegflqeatisvagcll
qffvfgslatdecfllavmaydrylaichplryphlmgpqwclglvltvw
lsgfmvdglvvalmaqlrfcgpnlvdhfycdfsplmvlacsdtqvaqvtt
fvlsvvfltvpfglvlisyaqivvtvlrvpsgtrrtkafstcsshlavvs
tfygtlmvlyivpsavhsqllskviallytvvtpifnpviytlmqevqqa
lalrrllyckptem
```

Human OR11A1 (SEQ ID NO: 9 DNA; SEQ ID NO: 10 PROTEIN)

SEQ ID NO: 9
```
atggaaattgtctccacaggaaacgaaactattactgaatttgtcctcct
tggcttctatgacatccctgaactgcatttcttgtttttattgtattca
ctgctgtctatgtcttcatcatcatagggaatatgctgattattgtagca
gtggttagctcccagaggctccacaaacccatgtatattttcttggcgaa
tctgtccttcctggatattctctacacctccgcagtgatgccaaaaatgc
tggagggcttcctgcaagaagcaactatctctgtggctggttgcttgctc
cagttctttatcttcggctctctagccacagctgaatgcttactgctggc
tgtcatggcatatgaccgctacctggcaatttgctaccactccactacc
cactcctgatggggcccagacggtacatggggctggtggtcacaacctgg
ctctctggatttgtggtagatggactggttgtggccctggtggcccagct
gaggttctgtggccccaaccacattgaccagttttactgtgactttatgc
ttttcgtgggcctggcttgctcggatcccagagtggctcaggtgacaact
ctcattctgtctgtgttctgcctcactattccttttggactgattctgac
atcttatgccagaattgtggtggcagtgctgagagttcctgctggggcaa
gcaggagaaggctttctccacatgctcctcccacctagctgtagtgacc
acattctatggaacgctcatgatcttttatgttgcaccctctgctgtcca
ttcccagctcctctccaaggtcttctccctgctctacactgtggtcaccc
ctctcttcaatcctgtgatctataccatgaggaacaaggaggtgcatcag
gcacttcggaagattctctgtatcaaacaaactgaaacacttgattga
```

SEQ ID NO: 10
```
Meivstgnetitefvllgfydipelhflffivftavyvfiiignmliiva
vvssqrlhkpmyiflanlsfldilytsavmpkmlegflqeatisvagcll
qffifgslataeclllavmaydrylaicyplhypllmgprrymglyyttw
lsgfvvdglvvalvaqlrfcgpnhidqfycdfmlfvglacsdprvaqvtt
lilsvfcltipfgliltsyarivvavlrypagasrrrafstcsshlavyt
tfygtlmifyvapsavhsqllskvfsllytvvtplfnpviytmmkevhqa
lrkilcikqtetld
```

Mouse Olfr740 (SEQ ID NO: 11 DNA; SEQ ID NO: 12 PROTEIN)

SEQ ID NO: 11
```
atgaaaaccttcagcagccccatcaactccagcaccaccactggcttcat
tctcttgggcttccctgccccagggagggcaaatcctcctctttgtgc
tcttctccattgtctacctgcttaccctcatgggcaacacttgcatcatc
tttgcagtatgctgggatcagagactccacacacccatgtacctactgct
ggccaacttctccttcctggagatctggtatgttacctccacagtcccca
acatgttggccaatttcctctctgacaccaaggtcatctctttctggatg
cttcctgcagttctatttcttcttctccttgggttctacagaatgccttt
cctggcagtcatggcatttgatcgataccttgccatctgtaggccacta
cattatcctgctctcatgactgggagcctctgcaacatccttgtgatcag
ttgctgggtgcttggtttcctctggttccctgttcccatcatcatcatct
cccagatgtccttctgtgggtccagaattatagaccacttcctgtgtgac
ccaggccctctattggccctcacctgttccagagcccattaatggaggt
tttctggacaattataacatctcttatcctgttcgttcctttcctcttca
tcatggatcttatacattggtcctgagagctgtgttcagagttccttca
agagatggacaaaaaaggctttctccacttgcggatctcatctcacagt
agttttactcttttatggctcagtgatgataatgtatctaagcccgacct
ctgagcatgaagctggaatgcagaagcttgtgactctattttattctgtg
gttactccactcattaatcctgtgatatacagtctgaggaacaaggatat
gaaacatgccctgcagaagattttaagaacataa
```

SEQ ID NO: 12
```
mktfsspinssttttgfillgfpcpregqillfvlfsivyllltlmgntcii
favcwdqrlhtpmylllanfsfleiwyvtstvpnmlanflsdtkvisfsg
cflqfyfffslgsteclflavmafdrylaicrplhypalmtgslcnilvi
scwvlgflwfpvpiiiisqmsfcgsriidhflcdpgpllaltcsraplme
vfwtiitslilfvpflfimgsytlvlravfrvpsrdgqkkafstcgshlt
vvllfygsvmimylsptseheagmqklvtlfysvvtplinpviyslrnkd
mkhalqkilrt
```

Human OR1A1 (SEQ ID NO: 13 DNA; SEQ ID NO: 14 PROTEIN)

SEQ ID NO: 13
```
atgagggaaaataaccagtcctctacactggaattcatcctcctgggagt
tactggtcagcaggaacaggaagattcttctacatcctcttcttgttca
tttaccccatcacattgattggaaacctgctcatcgtcctagccatttgc
tctgatgttcgccttcacaaccccatgtattttctccttgccaacctctc
cttggttgacatcttcttctcatcggtaaccatccctaagatgctggcca
accatctcttgggcagcaaatccatctctttttgggggatgcctaacgcag
```

-continued

```
atgtatttcatgatagccttgggtaacacagacagctatattttggctgc aatggcatatgatcgagctgtggccatcagccgcccacttcactacacaa caattatgagtccacggtcttgtatctggcttattgctgggtcttgggtg attggaaatgccaatgccctcccccacactctgctcacagctagtctgtc cttctgtggcaaccaggaagtggccaacttctactgtgacattacccct tgctgaagttatcctgttctgacatccactttcatgtgaagatgatgtac ctaggggttggcatttctctgtgccattactatgcatcattgtctccta tattcgagtcttctccacagtcttccaggttccttccaccaagggcgtgc tcaaggccttctccacctgtggttcccacctcacggttgtctctttgtat tatggtacagtcatgggcacgtatttccgccctttgaccaattatagcct aaaagacgcagtgatcactgtaatgtacacggcagtgaccccaatgttaa atcctttcatctacagtctgagaaatcgggacatgaaggctgccctgcgg aaactcttcaacaagagaatctcctcgtga
```

SEQ ID NO: 14
```
mrennqsstlefillgvtgqqeqedffyilflfiypitlignllivlaic sdvrlhnpmyfllanlslvdiffssvtipkmlanhllgsksisfggcltq myfmialgntdsyilaamaydravaisrplhyttimsprsciwliagswv ignanalphtlltaslsfcgnqevanfycditpllklscsdihfhvkmmy lgvgifsvpllciivsyirvfstvfqvpstkgvlkafstcgshltvvsly ygtvmgtyfrpltnyslkdavitvmytavtpmlnpfiyslrnrdmkaalr klfnkriss
```

Flag tag (SEQ ID NO: 15 DNA; SEQ ID NO: 16 PROTEIN)

SEQ ID NO: 15
```
gattacaaggacgacgacgataag
```

SEQ ID NO: 16
```
dykddddk
```

Rho tag (SEQ ID NO: 17 DNA; SEQ ID NO: 18 PROTEIN)

SEQ ID NO: 17
```
atgaacgggaccgagggcccaaacttctacgtgcctttctccaacaagac gggcgtggtg
```

SEQ ID NO: 18
```
mngtegpnfyvpfsnktgvv
```

Lucy tag (SEQ ID NO: 19 DNA; SEQ ID NO: 20 PROTEIN)

SEQ ID NO: 19
```
atgagaccccagatcctgctgctcctggccctgctgaccctaggcctggc
t
```

SEQ ID NO: 20
```
mrpqillllalltlgla
```

EXAMPLES

The below examples are illustrative only and are not meant to limit the claims or embodiments described herein.

Example 1

Figure 2:
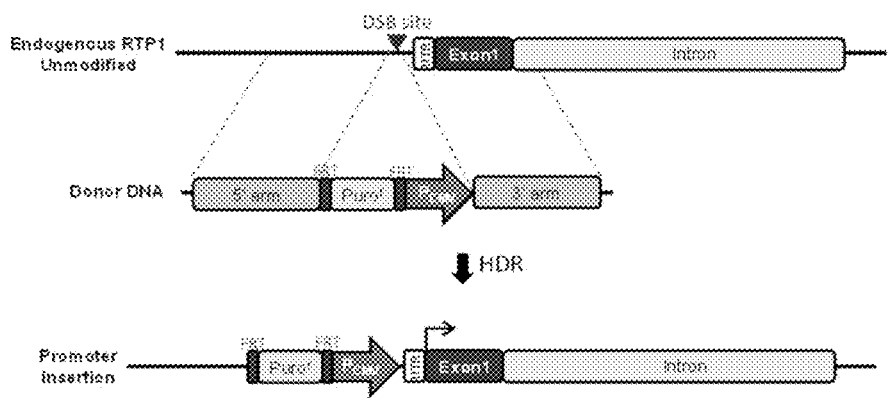
FIG. 2 shows a schematic of the CMV promoter insertion process.

Genome Editing Strategy to Induce Constitutive Activation of the Endogenous RTP1 Gene in HEK293T Cells A strategy to develop enhanced functional odorant receptor expression in heterologous expression system is described. Taking advantage of a newly available genome editing technology called CRISPR/Cas9, an endogenous RTP1 gene which is silent (inactive) in regular HEK293T cells, is specifically and constitutively activated by introducing a constitutive promoter (CMV) upstream of its coding sequence. FIG. 1) The RTP1 gene is located on chromosome 3 and the DNA sequence around its start site is shown. The Cas9 endonuclease is directed by a 20 base pair (bp) guide RNA (gRNA) homologous to the target. Upon delivery to the cells (GeneArt CRISPR Nuclease (CD4 enrichment) Vector Kit, cat #A21175) the guide RNA molecule and the Cas9 protein form an active complex that induces the desired double strand DNA break (DSB) upstream of the coding sequence. Boxes indicate the RTP1 gene on chromosome 3 (filled box, coding sequence (CDS); open box, untranslated region (UTR) in exon). The putative promoter region upstream of the RTP1 gene is inactive in HEK293T cells. The guide RNA target sequence (SEQ ID NO: 1) between position −150 and −131 and a Protospacer Adjacent Motif (PAM) from −153 to −151 from the start codon (ATG) respectively are shown. FIG. 1) DSB site for Cas9 nuclease 3 bp away from the PAM motif, specified by a triangle, allows a donor DNA (SEQ ID NO: 2) to be inserted. FIG. 2) A schematic of the CMV promoter insertion process is shown. The top configuration shows the RTP1 gene locus before modification and the bottom schematic shows the RTP1 locus after a donor DNA is targeted into the DSB site by Homology Directed Repair (HDR). The donor DNA is composed of a 5' homology arm, an FRT (Flippase Recognition Target)-flanked puromycin selection cassette, the CMV promoter and a 3' homology arm. The integration of the CMV promoter upstream of the RTP1 gene is then obtained by the cellular HDR mechanism inherent to eukaryotic cells. A donor plasmid containing two DNA stretches homologous to the sequences on either side of the desired entry point, flanking the puromycin resistance selection cassette (Puro$^r$) and the CMV DNA, is co-transfected into HEK293T cells. HDR results in the introduction of Puro$^r$ and CMV upstream of the RTP1 coding sequence. Puromycin selection cassette can be subsequently removed by the use of the Flippase enzyme.

Example 2

Selection of a Modified Cell Line Endogenously Expressing the RTP1 Gene

Figure 3:
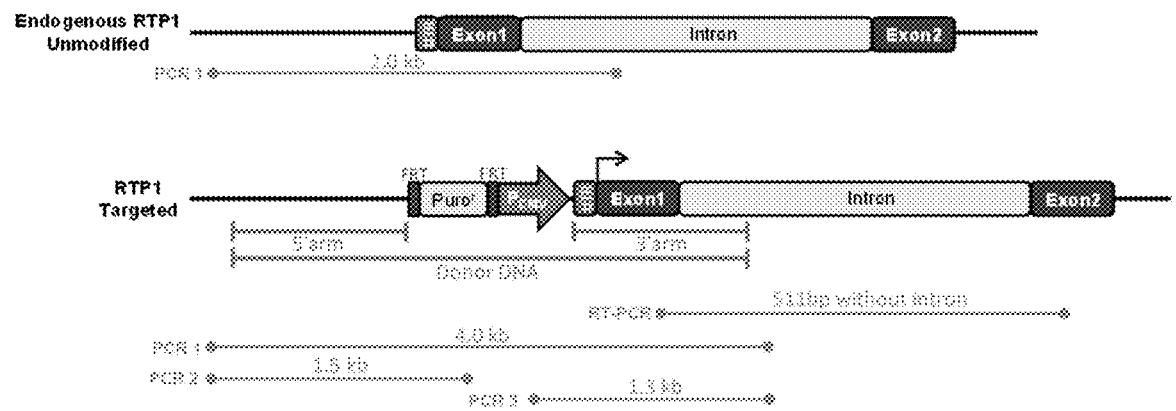
FIG. 3 shows a schematic of the wild type and recombined alleles and the corresponding genotyping regions.
Figure 4:
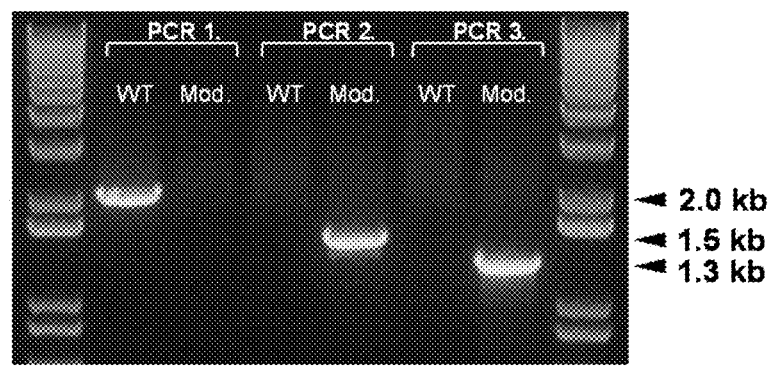
FIG. 4 shows the characterization of the CMV promoter integration in the engineered cell line.
Figure 5:
FIG. 5 shows the characterization of RTP1 mRNA expression in the engineered cell line.

Several control steps help to characterize the modification of the cell line and its integrity. FIG. 3) A schematic of the wild type and recombined alleles is shown. Grey lines indicate relative amplicon positions of PCR and RT-PCR experimental results for DNA genotyping and for RNA expression controls, respectively (not to scale). FIG. 4) The genomic DNA from the Puromycin resistant cell line is extracted and a PCR is performed that discriminates between non-recombined wild type (WT) and modified cell lines (Mod.). PCR 1 amplifies a 2.0 kb band only in wild type HEK293T cells but not in a modified cell line. The modified line should yield a 4.0 kb band with PCR1 but did not likely because of the length and the complexity of the genomic structure. Genotyping results for the modified cell line failed to produce the 2.0 kb band indicating a homozygous integration of the CMV promoter. Proper integration of the donor DNA was further tested with PCR 2 and 3, as indicated. FIG. 5) After mRNA extraction and cDNA synthesis, an RT-PCR experiment is performed to demonstrate that RTP1 mRNA is specifically expressed in the modified cell line but not in original HEK293T cells. This confirms that the CMV promoter that was integrated at the targeted genomic locus properly drives the expression of the RTP1 gene. The specificity of the RT-PCR bands was confirmed by direct sequencing of the amplified bands. Reverse-transcriptase negative (RT−) and GAPDH PCR conditions indicate the absence of contaminating genomic DNA and the presence of cDNA in all samples, respectively.

Example 3

Characterization of the RTP1 Protein Expression

Figure 6:
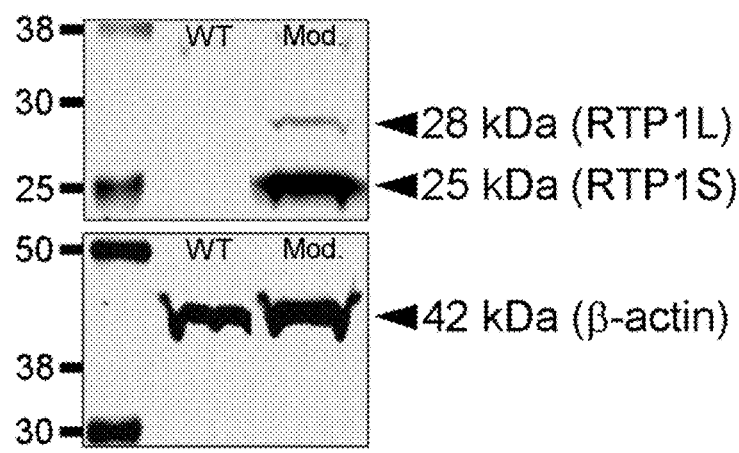
FIG. 6 shows the characterization of RTP1 protein expression in the engineered cell line.

RTP1 protein expression in the selected modified cell line was determined by western blot analysis using an RTP1-specific antibody. A long (RTP1L) and a short (RTP1S) protein form can originate from the endogenous RTP1 gene. The genome modification strategy described herein involved the introduction of the CMV promoter upstream of the RTP1L start codon to avoid any modification of the endogenous coding sequence; hence RTP1L was expected to be expressed. However the results indicate that the modified cell line was heavily biased towards the expression of RTP1S, suggesting that the endogenous RTP1 gene preferentially expresses the short version without further genome editing. The latter is the preferred version as it is known to better promote odorant receptor cell surface expression. FIG. 6) shows the western blots of RTP1 protein. Arrow heads indicate the expected protein sizes for RTP1S—25 kDa, RTP1L—28 kDa and the control protein β-actin—42 kDa. The absence of RTP1 protein in a wild type HEK293T cell line (WT) and the presence of RTP1S in the modified cell line (Mod.) are shown. Surprisingly a much stronger band for RTP1S compared to RTP1L can be seen. Membrane protein extraction was prepared according to the Mem-Per Plus membrane protein extraction kit (Pierce, cat #89842). Chameleon Duo Pre-stained used as size marker (LiCor, cat #92860000). Labelling was performed with the following primary antibodies: Rabbit anti-RTP1 (Invitrogen, cat #PA5-24028) and mouse anti-β-actin (Pierce, cat #PIMA515739). Detection was performed with the following secondary antibodies: goat anti-rabbit (LiCor cat #925-32211) and goat anti-mouse (LiCor cat #925-68070). Imaging was performed on an Odyssey CLx (LiCor).

Example 4

Figure 7:
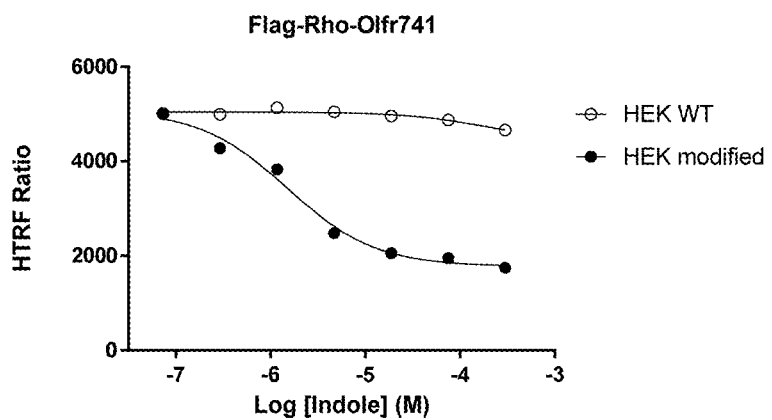
FIG. 7 shows a mouse receptor Olfr741 dose-response curve in the presence of increasing concentrations of indole.
Figure 8:
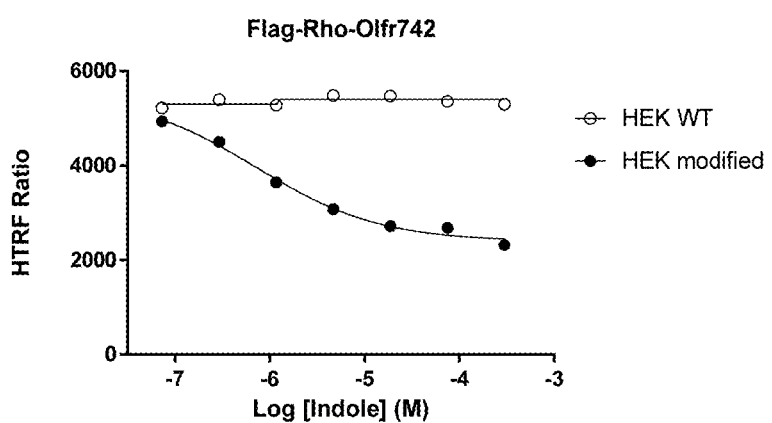
FIG. 8 shows a mouse receptor Olfr742 dose-response curve in the presence of increasing concentrations of indole.
Figure 9:
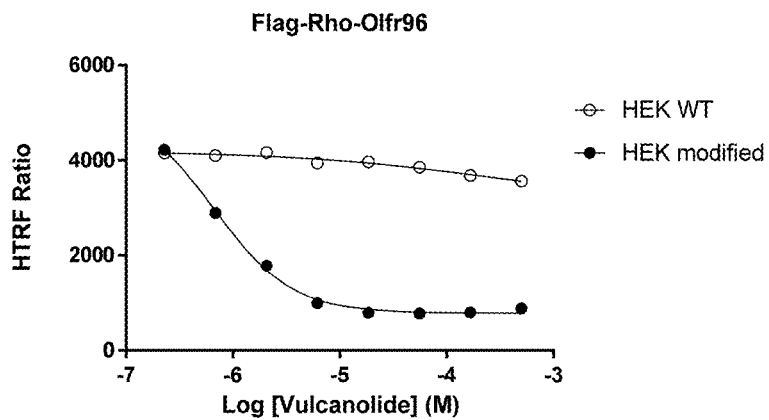
FIG. 9 shows a mouse receptor Olfr96 dose-response curve in the presence of increasing concentrations of vulcanolide.
Figure 10:
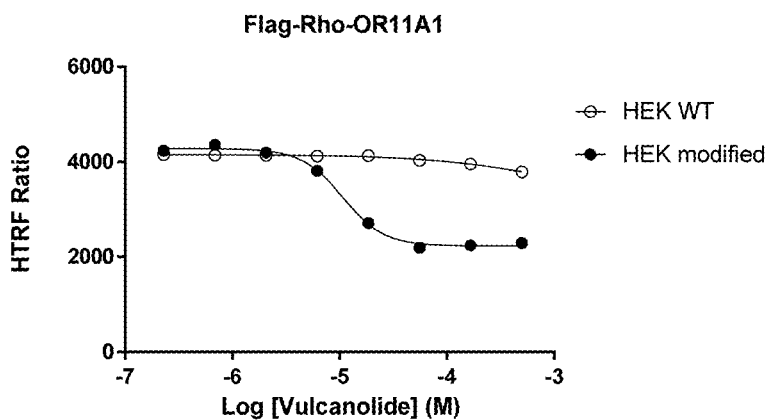
FIG. 10 shows a human receptor OR11A1 dose-response curve in the presence of increasing concentrations of vulcanolide.
Figure 11:
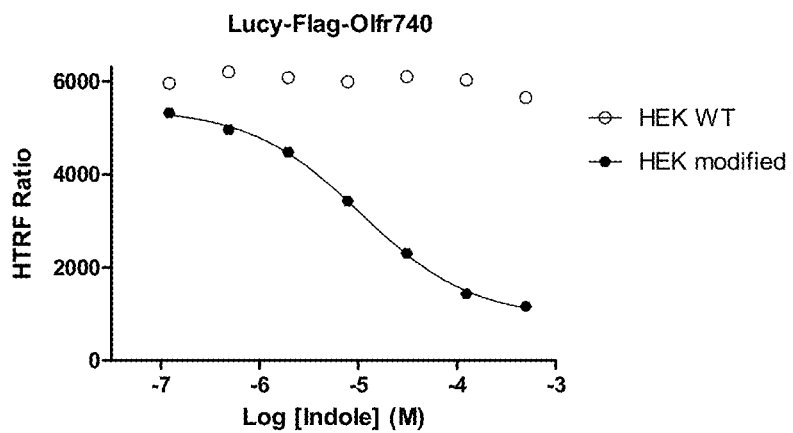
FIG. 11 shows a mouse receptor Olfr740 dose-response curve in the presence of increasing concentrations of indole.
Figure 12:
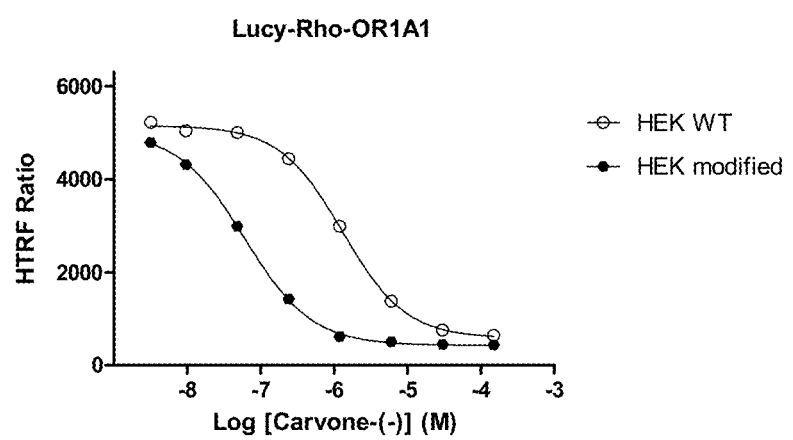
FIG. 12 shows a human receptor OR1A1 dose-response curve in the presence of increasing concentrations of carvone-(−).

Functional Characterization of Several Odorant Receptors in the Modified Cell Line Functional dose-response experiments were performed in order to evaluate the level of functional enhancement of activity of odorant receptors in the modified cell line. Odorant receptors were modified at their N-terminus with short polypeptide sequences or tags [e.g. Flag (SEQ ID NO: 15), Rho (SEQ ID NO: 17; 20 first amino acids of the bovine rhodopsin receptor), or Lucy (SEQ ID NO: 19)], transiently expressed in WT or modified HEK293T cells, and stimulated with odorant compounds to determine the activity of the receptors. FIGS. 7 and 8) Using a cell-based odorant binding assay, the activity of Olfr741 (SEQ ID NO: 4) and Olfr742 (SEQ ID NO: 6) to indole was tested in the engineered RTP1 cell line and compared to HEK293T lacking RTP1 protein expression. Odorant receptors were transfected into both cell lines and exposed to increasing concentrations of indole. Odorant-induced activity was detected by measuring the level of cAMP increase in the cytosol using an HTRF based kit (CisBio, cAMP dynamic 2 kit, cat #62AM4PEJ). FIGS. 9 and 10) Using the same cell-based odorant binding assay, the activity of Olfr96 (SEQ ID NO: 8) and OR11A1 (SEQ ID NO: 10) to vulcanolide was tested in the engineered RTP1 expressing cell line and compared to HEK293T lacking RTP1 protein expression. The activity of Olfr740 (SEQ ID NO: 12) to indole was also tested in both cellular backgrounds. A dose-dependent increase of receptor activity is recorded for all ORs in the modified RTP1 cell line and not in the unmodified control cell line lacking RTP1 expression. Furthermore, the activity of OR1A1 (SEQ ID NO: 14) to carvone-(−) was tested in both cellular backgrounds. Even though OR1A1 can be expressed in regular HEK293T, a more potent dose-dependent increase of receptor activity is recorded in the modified RTP1 cell line and compared to the unmodified control cell line lacking RTP1 expression.

What is claimed is:

1. An isolated human or mouse cell whose genome comprises an endogenous nucleic acid sequence encoding a wild-type receptor transporting protein 1 (RTP1) operably linked to an exogenous constitutive or inducible promoter, wherein said cell is capable of functionally expressing the wild-type RTP1.

2. The cell as recited in claim 1 wherein the cell is a non-olfactory cell.

3. The cell as recited in claim 2 wherein the cell is derived from a HEK293T cell line.

4. The cell as recited in claim 1 further comprising a nucleic acid sequence encoding an odorant receptor, wherein said cell is capable of functionally expressing the odorant receptor.

5. The cell as recited in claim 4, wherein the odorant receptor is selected from the group consisting of an indole, skatole, and musk odorant receptor.

6. A method of making the isolated human or mouse cell of claim 4, the method comprising introducing:
   i) guide RNA (gRNA) that targets upstream of an endogenous RTP1 gene,
   ii) Cas nuclease,
   iii) donor DNA comprising the exogenous constitutive or inducible promoter, and
   iv) a nucleic acid sequence encoding an odorant receptor into an isolated human or mouse cell such that the isolated human or mouse cell of claim 4 is obtained.

7. The cell as recited in claim 1 wherein the promoter is a CMV promoter.

8. A method of making the isolated human or mouse cell of claim 1, the method comprising introducing:
   i) guide RNA (gRNA) that targets upstream of an endogenous RTP1 gene,
   ii) Cas nuclease, and
   iii) donor DNA comprising the exogenous constitutive or inducible promoter,
into an isolated human or mouse cell such that the isolated human or mouse cell of claim 1 is obtained.

9. The method of claim 8, wherein the Cas nuclease is Cas9.

10. The method as recited in claim 9 wherein the Cas9 protein is selected from the group consisting of Cas9 and Cas9 nickase.

11. A method of using the isolated human or mouse cell of claim 1 for identifying compounds that modulates the activity of an odorant receptor, the method comprising:
   a) contacting the cell of claim 4 with a compound,
   b) determining whether the compound modulates activity of the odorant receptor.

12. The method of claim 11, odorant receptor is selected from the group consisting of an indole, skatole, and musk odorant receptor.

13. An isolated human cell whose genome comprises an endogenous nucleic acid sequence encoding a wild-type receptor transporting protein 1 (RTP1) operably linked to an exogenous constitutive or inducible promoter, wherein said cell is capable of functionally expressing the wild-type RTP1.

* * * * *